US010851393B2

(12) United States Patent
San et al.

(10) Patent No.: US 10,851,393 B2
(45) Date of Patent: Dec. 1, 2020

(54) KAS-III FREE FA SYNTHESIS

(71) Applicant: WILLIAM MARSH RICE UNIVERSITY, Houston, TX (US)

(72) Inventors: Ka-Yiu San, Houston, TX (US); Xian Zhang, Houston, TX (US); Hui Wu, Houston, TX (US); Dan Wang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 45 days.

(21) Appl. No.: 15/553,129

(22) PCT Filed: Feb. 22, 2016

(86) PCT No.: PCT/US2016/018963
§ 371 (c)(1),
(2) Date: Aug. 23, 2017

(87) PCT Pub. No.: WO2016/137897
PCT Pub. Date: Sep. 1, 2016

(65) Prior Publication Data
US 2018/0148746 A1 May 31, 2018

Related U.S. Application Data
(60) Provisional application No. 62/120,232, filed on Feb. 24, 2015.

(51) Int. Cl.
| | |
|---|---|
| *C12N 1/21* | (2006.01) |
| *C12N 9/04* | (2006.01) |
| *C12N 9/02* | (2006.01) |
| *C12N 9/10* | (2006.01) |
| *C12N 9/88* | (2006.01) |
| *C12N 9/16* | (2006.01) |
| *C12P 7/64* | (2006.01) |
| *C12N 1/20* | (2006.01) |

(52) U.S. Cl.
CPC .............. *C12P 7/6409* (2013.01); *C12N 1/20* (2013.01); *C12N 9/0006* (2013.01); *C12N 9/1029* (2013.01); *C12N 9/13* (2013.01); *C12N 9/16* (2013.01); *C12N 9/88* (2013.01); *C12P 7/6463* (2013.01); *C12Y 101/011* (2013.01); *C12Y 103/01009* (2013.01); *C12Y 203/01041* (2013.01); *C12Y 208/03008* (2013.01); *C12Y 301/02014* (2013.01); *C12Y 402/01017* (2013.01)

(58) Field of Classification Search
None
See application file for complete search history.

(56) References Cited

U.S. PATENT DOCUMENTS

| | | | |
|---|---|---|---|
| 7,709,261 B2 | 5/2010 | San | |
| 7,901,924 B2 | 3/2011 | San | |
| 8,236,525 B2 | 8/2012 | San | |
| 8,486,686 B2 | 7/2013 | Segueilha | |
| 8,709,753 B2 | 4/2014 | San | |
| 8,795,991 B2 | 8/2014 | San | |
| 8,906,667 B2 | 12/2014 | San | |
| 2010/0242345 A1* | 9/2010 | Keasling | C10L 1/026 44/388 |
| 2011/0166370 A1* | 7/2011 | Saunders | C12N 9/90 554/1 |
| 2012/0070868 A1* | 3/2012 | Lee | C12N 9/0006 435/134 |
| 2013/0267012 A1* | 10/2013 | Steen | C12N 15/81 435/254.21 |
| 2013/0323766 A1* | 12/2013 | Sillers | C12N 1/22 435/15 |
| 2014/0093921 A1 | 4/2014 | San | |
| 2014/0193867 A1 | 7/2014 | San | |
| 2014/0212935 A1 | 7/2014 | San | |
| 2014/0273114 A1 | 9/2014 | San | |
| 2016/0168603 A1* | 6/2016 | Garg | C12N 9/1029 435/134 |

FOREIGN PATENT DOCUMENTS

WO   WO-2008119082 A2 * 10/2008   ............... C12N 9/16

OTHER PUBLICATIONS

Lai et al., Beta-ketoacyl-acyl carrier protein synthase III (FabH) is essential for bacterial fatty acid synthesis, J. Biol. Chem., 2003, 278, 51494-503.*
Showman, Metabolomics based gene function annotation in *Escherichia coli* and Methanosarcina acetivorans with genetic gain- or loss-of-function strains, Dissertation, Iowa State University, 2014.*
Torella et al., Tailored fatty acid synthesis via dynamic control of fatty acid elongation, Proc. Natl. Acad. Sci., 2013, 110, 11290-95.*
Yao et al., Regulation of cell size in response to nutrient availability by fatty acid biosynthesis in *Escherichia coli*, Proc. Natl. Acad. Sci. USA Plus, 2012, E2561-68.*
Uniprot, Accession No. P14611, 2014, www.uniprot.org.*
Uniprot, Accession No. P23608, 2014, www.uniprot.org.*

(Continued)

*Primary Examiner* — Robert B Mondesi
*Assistant Examiner* — Todd M Epstein
(74) *Attorney, Agent, or Firm* — Boulware & Valoir

(57) ABSTRACT

The present disclosure describes a genetically engineered a KASIII-independent fatty acid biosynthetic pathway that makes use of the promiscuous nature of the rest of the FAS enzymes (3-ketoacyl-ACP synthetase, 3-ketoacyl-ACP reductase, 3-hydroxyacyl ACP dehydrase, enoyl-ACP reductase) to bypass the KASIII step by providing a Co-A precursor of two or higher than two carbons (such as the four carbon butyryl-CoA) as the starting molecule. Since many CoA-based starter molecules can be supplied for the fatty acid synthesis, much more diversified products can be obtained with various carbon-chain lengths. As such, this disclosure will serve as a powerful and efficient platform to produce low to medium chain length products carrying many different functional groups.

17 Claims, 16 Drawing Sheets

(56) References Cited

OTHER PUBLICATIONS

Zhang et al., Enhancing fatty acid production by the expression of the regulatory transcription factor FadR, Metabolic Eng., 2012, 14, 653-60.*
Chen et al., Engineering redox balance through cofactor systems, Trends Biotechnol., 2014, 32, 337-43.*
Horswill et al., Characterization of the Propionyl-CoA Synthetase (PrpE) Enzyme of *Salmonella enterica*, Biochemistry, 2002, 41, 2379-87.*
Denoya et al., A Second Branched-Chain a-Keto Acid Dehydrogenase Gene Cluster (bkdFGH) from Streptomyces avermitilis, J. Bacteriol., 1995, 177, 3504-11.*
Zhang X., Li M., Agrawal A., San K. Efficient free fatty acid production in *Escherichia coli* using plant acyl-ACP thioesterases. Metab. Eng. 2011, 13: 713-722.
Nathan L. Alderson et al., The Human FA2H Gene Encodes a Fatty Acid 2-Hydroxylase. J. Biol. Chem. 2004, 279: 48562-48568.
N. Nakashima & T. Tamura Gene silencing in *Escherichia coli* using antisense RNAs expressed from doxycycline-inducible vectors. Letters in Applied Microbiology.2013, 56: 436-442.
Jaoon Y. H. Kim & Hyung Joon Cha Down-regulation of acetate pathway through antisense strategy in *Escherichia coli*: improved foreign protein production. Biotechnol Bioeng, 2003, 83(7): 841-853.
Srivastava A., et al, 14-Aminotetradecanoic acid exhibits antioxidant activity and ameliorates xenobiotics-induced cytotoxicity. Mol. Cell. Biochem. 2012, 364: 1-9.
Jing et al., Phylogenetic and experimental characterization of an acyl-ACP thioesterase family reveals significant diversity in enzymatic specificity and activity, BMC Biochemistry 2011, 12:44.

* cited by examiner

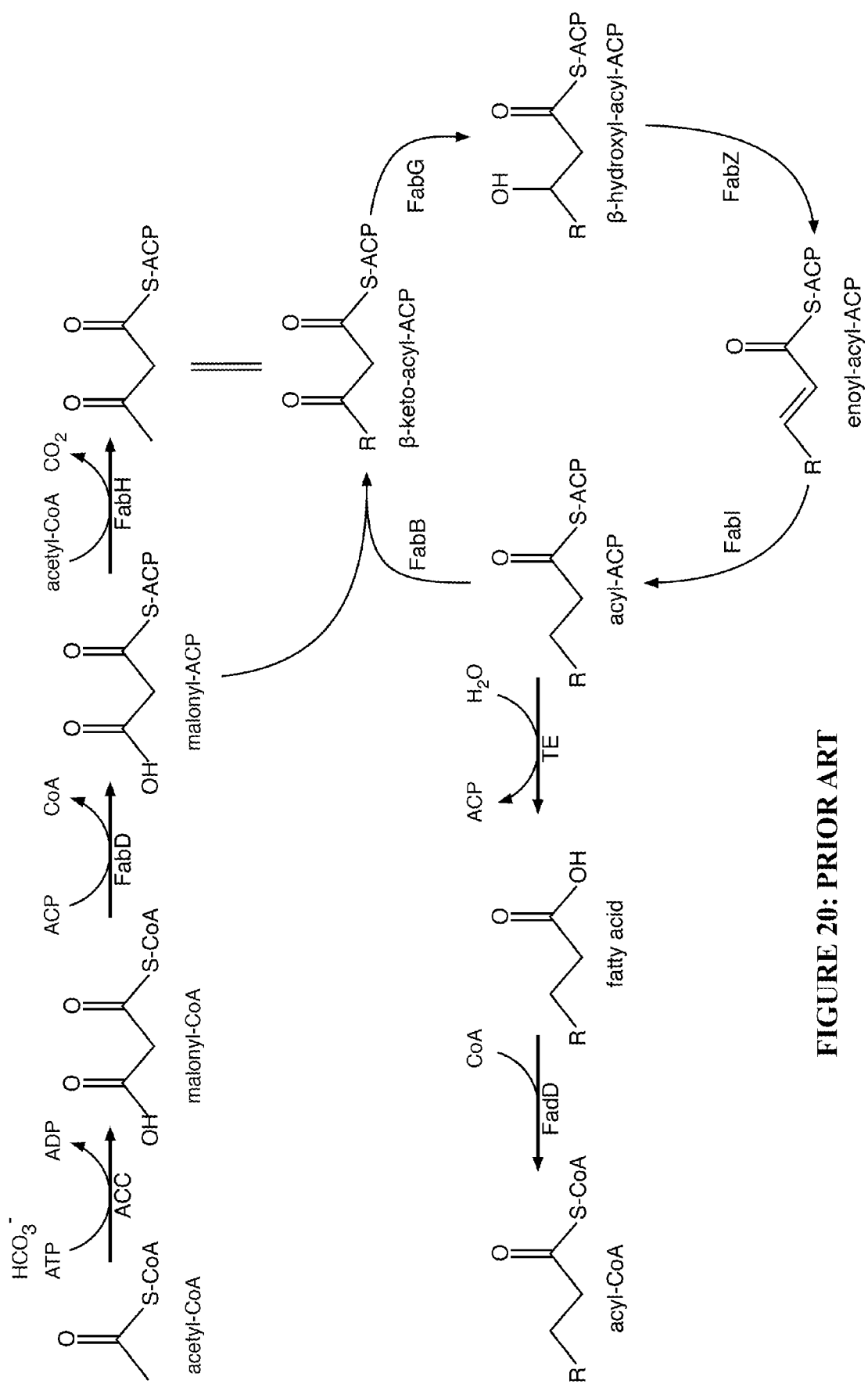
FIGURE 20: PRIOR ART

KAS-III FREE FA SYNTHESIS

PRIOR RELATED APPLICATIONS

This application claims priority to U.S. App. No. 62/120,232, filed Feb. 24, 2015, and PCT App. No. PCT/US16/18963, filed Feb. 22, 2016, each of which are expressly incorporated by reference in its entirety for all purposes.

FEDERALLY SPONSORED RESEARCH STATEMENT

This invention was made with government support under Grant Nos: 2012-10008-20263 and OTT-SRA-13072503 awarded by the USDA. The government has certain rights in the invention.

FIELD OF THE DISCLOSURE

The invention relates to microbial product of products using a KASIII-independent FAS pathway and primers or starter molecules that are either supplied to the cell or made by the cell.

BACKGROUND OF THE DISCLOSURE

Fatty acids are aliphatic acids fundamental to energy production and storage, cellular structure and as intermediates in the biosynthesis of hormones and other biologically important molecules. Fatty acids in *E. coli*, for example, are synthesized by a series of decarboxylative Claisen condensation reactions using acetyl-CoA to add two carbon units to a growing fat. Following each round of elongation the beta keto group is reduced to the fully saturated carbon chain by the sequential action of a ketoreductase, a dehydratase, and an enol reductase. The growing fatty acid chain is carried between these active sites while attached covalently to the phosphopantetheine prosthetic group of an acyl carrier protein (ACP), and is released from the ACP by the action of a thioesterase (TE) upon reaching a carbon chain length of e.g., 16, although this can be varied by adding different TE enzymes to the cell. See FIG. 20.

There are two principal classes of fatty acid synthases. Type I systems utilize a single large, multifunctional polypeptide and are common to both mammals and fungi. A Type I fatty acid synthase system is also found in the CMN group of bacteria (Corynebacteria, Mycobacteria, and *Nocardia*). In these bacteria, the FAS I system produces palmitic acid, and cooperates with the FAS II system to produce a greater diversity of lipid products.

Type II fatty acid synthase (FASII) is present in prokaryotes, plants, fungi, and parasites, as well as in mitochondria. FASII is characterized by the use of the discrete, monofunctional enzymes for fatty acid synthesis. In contrast to the complex Type I fatty acid synthase that catalyzes multiple enzymatic steps, FASII uses individual enzymes to carry out the same steps.

In the Type II system, fatty acid elongation occurs in two-carbon steps by the Claisen condensation of acetyl coA and malonyl-ACP (ACP is acyl carrier protein, a small, acidic, soluble protein that shuttles the elongating chain between enzymes). Three enzymes (FabB, FabF, and FabH) catalyze these condensation reactions, and a number of other enzymes perform additional necessary reactions within the pathway.

The substrate specificity of the initial reaction, catalyzed by FabH, aka KASIII, is quite limited. In the case of FabH, the substrates are malonyl-ACP and acetyl-CoA, initiating the first cycle of chain elongation during fatty acid biosynthesis. The activity of FabH with propionyl-CoA is as good as with acetyl-CoA, leading to the formation of fatty acids with an uneven number of carbon atoms. However, the activity with butyryl-CoA is much lower, and hexanoyl-CoA is not a substrate of FabH. Further, the *E. coli* FabH exhibits no activity with branched-chain acyl-CoA esters. Due to this limited substrate specificity, the products produced by the normal FAS pathway are quite limited.

If the entry point into the two carbon elongation pathway of the FAS cycle could be opened up, it would be possible to make a much broader range of products using the FAS enzymes. This disclosure is directed to such bacteria, methods, and products produced thereby.

SUMMARY OF THE DISCLOSURE

Normally, in fatty acid synthesis by microbes, the first step is β-Ketoacyl-acyl carrier protein (ACP) synthase III (KASIII, also called acetoacetyl-ACP synthase) encoded by the fabH gene (in *E. coli* and several other bacteria), which catalyzes the first elongation reaction of type II fatty acid synthesis in bacteria and plant plastids. This enzyme has very strict substrate specificity requirements, and thus, other precursors cannot enter the fatty acid synthesis (FAS) pathway for sequential 2-carbon elongation. Thus, the wild type FAS pathway cannot be used to make a diverse set of products.

We genetically engineered a KASIII-independent fatty acid biosynthetic pathway, making use of the promiscuous nature of the rest of the FAS enzymes (3-ketoacyl-ACP synthetase, 3-ketoacyl-ACP reductase, 3-hydroxyacyl ACP dehydrase, enoyl-ACP reductase) to bypass the FASIII step by providing atypica Co-A precursors (such as the four carbon butyryl-CoA) as the starting molecule. Since many CoA-based starter or primer molecules can be supplied for the fatty acid synthesis if the KASIII step is bypassed, much more diversified products can be obtained with various carbon-chain lengths. As such, this disclosure will serve as a powerful and efficient platform to produce low to medium chain length products carrying many different functional groups. Of course, the normal 2 and 3 carbon units can also be fed into the pathway, but the main advantage herein lies in producing atypical FAS products.

The advantages of this KASIII-independent fatty acid synthesis system include one or more of the following:

The system makes use of promiscuous nature of the rest of the fatty acid synthesis system and bypasses the highly specific KASIII enzyme.

The system uses abundant CoA with different starter molecules to make a variety of primers.

A very diverse group of fatty acid derivatives, such as hydroxy fatty acids, dicarboxylic fatty acids, amino fatty acids, halogenated fatty acids, unsaturated fatty acids, bifunctional fatty acids, and the like can be produced (in particular, with omega functional groups, such as the omega-hydroxy fatty acids or omega-amino fatty acids) by supplying the desired primer molecules to the cells. Starter molecules can be supplied externally and then activated by CoA-synthetase or CoA transferase, or primers can be produced in vivo by introducing the necessary metabolic pathways.

The KASIII independent fatty acid synthesis system can co-exist with the existing KASIII dependent system. For higher yields, the native KASIII can be downregulated or a null mutant can be provided.

The KASIII independent fatty acid synthesis uses both CoA and ACP as the carrier and hence will be more efficient that other non-FAS-based pathways.

The KASIII independent fatty acid synthesis system opens the windows for KAS I and KAS II enzymes to be optimized either through the use of these genes/enzymes from various organisms or through protein engineering.

By a "KASIII-independent fatty acid synthesis" pathway, we refer to a pathway to make fatty acids and other products using the normal FAS enzymes, but by-passing the first KASIII (or equivalent) enzyme thus avoiding its strict substrate specificity. The KASIII enzyme is avoided by providing the cells with a 2, >2, >3, >4 or higher carbon precursor, or by providing the cells with the added overexpressed enzymes to allow them to make their own e.g., 4 carbon precursors.

By "KASIII" we mean the β-Ketoacyl-Acyl Carrier Protein Synthase III, encoded by fabH in *E. coli*, but possibly having other gene names in other species. See e.g. EC 2.3.1.180 and the Brenda entry at brenda-enzymes.org/enzyme.php?ecno=2.3.1.180, incorporated by reference herein in its entirety for all purposes.

By "primer" herein, we mean a CoA-activated molecule that can enter the FAS cycle for elongation. A "starter molecule" is similar, but has to be activated by coA to become a primer. Several primers and/or starter molecules are exemplified herein. Once the functionalized primer starts the FAS cycle, further two carbon additions can use acetyl-CoA per the normal FAS cycle, but the first one is typically functionalized to produce functionalized fatty acid products.

Note, that once the functionalized primer has entered the FAS cycle, acetyl Co-A is used for further elongation, and thus in this context, the functionalized primer refers only to the initiating primer, not the later used "acetyl-CoA elongation units."

By "functionalized" fatty acids, we mean an atypical fat not normally produced by the FAS cycle, that has an added group, such as a halogen, amino, hydroxy, branched backbone, unsaturated fatty acids, especially in the omega position, difunctional groups, such a dicarboxylates, and the like. Functionalized fats can be made herein by adding a functionalized primer or functionalized starter molecule to a cell having a KASIII-independent FAS cycle. In addition, functionalized fats can be made by enzyme modification after the fat is made. Both approaches are exemplified herein.

In some cases, a set of FAS enzymes are added with substrate specificity so as to take a functionalized primer through the first round of the FAS cycle. In other instances, the native FAS genes will suffice. This will depend on the substrate specificity of the native FAS genes, as well as on the identity of the functionalized primer. Both are exemplified herein. Even where the native FAS enzymes have the requisite substrate specificity, it still may be desired to overexpress one or all of the FAS enzymes, because this can increase yields. However, it is not essential, and the bacteria exemplified herein still make fats.

It is not essential to delete or down regulate the native KASIII and the two pathways can co-exist. However, reducing or knocking out the native KASIII gene can improve yields. Both are exemplified herein.

The invention includes one or more of the following embodiments in and combination(s) thereof:

---

A method of making functionalized fatty acids, comprising:
a) growing a genetically engineered microbe in a medium for a time sufficient to allow production of a functionalized fatty acid, said microbe comprising:
i) a β-ketoacyl-acyl carrier protein synthase III (KASIII) independent fatty acid synthesis (FAS) pathway that makes a product from a functionalized primer (excluding acetyl-CoA or propionyl-coA) using FAS enzymes (except for KASIII);
ii) said microbe having an overexpressed acyl ACP thioesterase (TE);
iii) said microbe having one or more (or all) overexpressed enzymes selected from the group consisting of a 3-ketoacyl-ACP synthetase, a 3-ketoacyl-ACP reductase, a 3-hydroxyacyl ACP dehydrase, a enoyl-ACP reductase, and a Co-A transferase; and
b) isolating said functionalized fatty acid, wherein said functionalized fatty acid is a branched fatty acid, a hydroxy fatty acid, a halogenated fatty acid, an unsaturated fatty acid, or an amino fatty acid.

A method of making a product;
a) growing any microbe as herein described in a medium allowing cell growth;
b) elongating a starter or primer molecule or primer molecule having 2 or >2 carbons using the FAS enzymes (except for KASIII) to make a product; and
c) isolating said product.

A method of making a product, comprising growing any microbe described herein in a medium; elongating a starter or primer molecule having 2 or more carbons using the FAS enzymes (except for KASIII) to make a product; and isolating said product.

Any method as herein described, comprising adding said starter molecule or primer molecule to said medium.

Any method as herein described, wherein a functionalized primer or functionalized starter molecule for fatty acid synthesis is added to the medium.

Any method as herein described, wherein a functionalized starter molecule is added to said medium, and wherein said microbe comprises one or more overexpressed enzymes for activating said functionalized starter molecule with CoA to make a functionalized primer molecule, such as coA synthestase or coA transferase. Other examples are described herein.

Any method as herein described, wherein a functionalized primer is made by said microbe and said microbe also comprises one or more overexpressed enzymes for synthesizing said functionalized primer, such as EC 2.3.1.9 thiolase; EC 1.1.1.157 hydroxybutyryl-CoA dehydrogenase; EC 4.2.1.17 crotonase or enoyl-CoA hydratase and EC 1.3.99.2 butyryl-CoA dehydrogenase or EC 1.3.1.44 trans-2-enoyl-CoA reductase, or any of the enzymes specified herein.

Any method or microbe as herein described, wherein said microbe comprises a reduced activity of KASIII (KASIII-) or a null mutant of fabH (ΔKASIII).

Any method or microbe as herein described, the microbe comprising i) overexpressed PhaA (β-ketothiolase), PhaB (acetoacetyl-CoA reductase), TER (trans-enoyl-coenzyme A reductase), and FabZ (3-hydroxyacyl-ACP dehydrase) or Crt (crotonase), or an expression construct(s) overexpressing these enzymes; or ii) overexpressed propionyl-CoA synthase (PrpE) or an expression construct overexpressing that enzyme.

A genetically engineered microbe comprising:
a) a β-ketoacyl-acyl carrier protein synthase III (KASIII) independent fatty acid synthesis (FAS) pathway that makes a product from a primer excluding acetyl coA or propionyl-coA using FAS enzymes (except for KASIII);
b) said microbe having an overexpressed acyl ACP thioesterase (TE);
c) said microbe also having one or more expression vectors overexpressing enzymes selected from the group consisting of 3-ketoacyl-ACP synthetase, 3-ketoacyl-ACP reductase, 3-hydroxyacyl ACP dehydrase, enoyl-ACP reductase, and Co-A transferase.

A method or microbe as herein described, wherein said primer is produced in vivo by a native pathway or by a genetically engineered pathway.

A method or microbe as herein described, wherein said primer or a starter molecule for said primer is supplied to said microbe in a medium for growing said microbe.

A method or microbe as herein described, wherein said product is selected from the group consisting of C6-C16 hydroxy fatty acids, C6-C16 amino fatty acids, C6-C16 halogenated fatty acids, C6-C16 branched fatty acids, C6-C16 unsaturated fatty acids, or C6-C16 ω-hydroxy fatty acids, or derivatives thereof.

A method or microbe as herein described, wherein said product is C6-C16 ω-hydroxy fatty acids or derivatives thereof.

A method or microbe as herein described, wherein bifunctional α,ω-dicarboxylic acids are obtained by the oxidation of said ω-hydroxy fatty acids.

A method or microbe as herein described, wherein bifunctional α,ω-diols are obtained by the reduction of said ω-hydroxy fatty acids.

A method or microbe as herein described, further comprising manipulating one or more of genes involved in (1) carbon uptake and glycolysis such as ptsG, (2) TCA cycle such as sucC, (3) various transcription factors regulating such as Crp-CAMP, Rpos, etc (4) cofactor balance such as NAD/NADH, NADP/NADPH, and CoA/acetyl-CoA, and (5) fatty acid synthesis such as fabB, fabF, fabG, fabI and/or fabZ or their equivalents from antibiotic synthesis pathway of *Streptomyces* to improve product production.

A genetically engineered microbe having a KASIII-independent FAS pathway that makes a product from a primer using FAS enzymes (except for KASIII), said microbe having an expression vector(s) overexpressing a TE, a 3-ketoacyl-ACP synthetase, a 3-ketoacyl-ACP reductase, a 3-hydroxyacyl ACP dehydrase, an enoyl-ACP reductase, and a Co-A transferase with specificity for said primer.

A genetically engineered microbe having a KASIII-independent FAS pathway that makes a product from a primer using FAS enzymes (except for KASIII), said microbe having an expression vector(s) overexpressing a TE, a 3-ketoacyl-ACP synthetase, a 3-ketoacyl-ACP reductase, a 3-hydroxyacyl ACP dehydrase, a enoyl-ACP reductase, and a Co-A transferase with specificity for said primer, said microbe further having KASIII- or ΔKASIII.

A genetically engineered microbe having a β-ketoacyl-acyl carrier protein synthase III (KASIII) independent fatty acid synthesis (FAS) pathway that makes a product from a starter molecule of >2 carbons or >3 carbons using FAS enzymes (except for KASIII).

A method of microbe as herein described, said microbe having one or more overexpressed enzymes selected from the group consisting of 3-ketoacyl-ACP synthetase, 3-ketoacyl-ACP reductase, 3-hydroxyacyl ACP dehydrase, enoyl-ACP reductase, acyl ACP thioesterase or Co-A transferase.

A method or microbe as herein described, where a product is selected from the group consisting of fatty acids, hydroxy fatty acids, amino fatty acids, halogenated fatty acids, branched fatty acids or a ω-hydroxy fatty acids, α,ω-dicarboxylic acids, α,ω-diol fatty acids.

A method of microbe as herein described, said microbe further comprising reduced native acyl-carrier protein (ACP) dependent fatty acid biosynthesis, malonyl-CoA-ACP transacylase, acetyl-CoA carboxylase or KASIII.

A method or microbe as herein described, comprising manipulating one or more of genes involved in (1) carbon uptake and glycolysis such as ptsG, (2) TCA cycle such as sucC, (3) various transcription factors regulating such as Crp-CAMP, Rpos, etc. (4) cofactor balance such as NAD/NADH, NADP/NADPH, and CoA/acetyl-CoA, and (5) fatty acid synthesis such as fabB, fabF, fabG, fabI and/or fabZ or their equivalents from antibiotic synthesis pathway of *Streptomyces* to improve product production.

A genetically engineered microbe having a KASIII-independent FAS pathway that makes a product from a starter molecule of >2 carbons using FAS enzymes, said microbe having one or more overexpressed enzymes selected from the group consisting of 3-ketoacyl-ACP synthetase, 3-ketoacyl-ACP reductase, 3-hydroxyacyl ACP dehydrase, enoyl-ACP reductase, thioesterase or Co-A transferase.

A genetically engineered microbe having KASIIII-independent FAS pathway that makes a product from a starter molecule of >3 carbons using FAS enzymes, said microbe having one or more overexpressed enzymes selected from the group consisting of 3-ketoacyl-ACP synthetase, 3-ketoacyl-ACP reductase, 3-hydroxyacyl ACP dehydrase, enoyl-ACP reductase, thioesterase or Co-A transferase.

A recombinant bacteria comprising KASIII⁻, TE⁺, PhaA⁺, PhaB⁺, TER⁺, and either FabZ⁺ or crt⁺ (or the enzymes with the equivalent activity). Any bacteria, further comprising PrpE⁺ (or the enzyme with the equivalent activity).

NOTE:
Any single detail herein described can be combined with any other one or more details for claiming purposes, as to list all possible combinations of details that can be claimed would serve no purpose other than to make the disclosure inordinately lengthy.

Generally speaking, we have referenced protein names herein and included EC numbers for accurate identification, but it is understood that a change in protein activity can of course be effected by changing the gene. This provides clarity since the gene nomenclature can be widely divergent in bacteria, but the proteins are defined by their activities and EC numbers.

Once an exemplary protein is obtained, e.g., in *E. coli*, which is completely sequenced and is the workhorse of genetic engineering and bioproduction, many additional examples proteins of similar activity can be identified by BLAST search. Further, every protein record is linked to a gene record, making it easy to design expression or overexpression vectors. Many of the needed enzymes are already available in vectors, and can often be obtained from cell depositories or from the researchers who cloned them. But, if necessary, new clones can be prepared based on available sequence information using RT-PCR techniques or chemical synthesis. Thus, it should be easily possible to obtain all of the needed enzymes for overexpression.

Understanding the inherent degeneracy of the genetic code allows one of ordinary skill in the art to design multiple nucleotides that encode the same amino acid sequence. NCBI provides codon usage databases for optimizing DNA sequences for protein expression in various species. Using such databases, a gene or cDNA may be "optimized" for expression in *E. coli*, or other bacterial species using the codon bias for the species in which the gene will be expressed.

Initial cloning experiments may have proceeded in *E. coli* for convenience since most of the required genes were already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella*, and *Streptococcus*, or any of the completely sequenced bacterial species. Indeed, thousands of bacterial genomes have been completely sequenced, and this information greatly simplifies both the generation of vectors encoding the needed genes, as well as the planning of a recombinant engineering protocol. Such species are listed along with links at http://en.wikipedia.org/wiki/List_of_sequenced_bacterial_genomes, incorporated by reference herein in its entirety for all purposes.

Additionally, yeast is a common species used for microbial manufacturing, and many species can be successfully transformed. In fact, rat acyl ACP thioesterase has already been successfully expressed in yeast *Saccharomyces*, as have bacterial FAS genes. Other species include but are not limited to *Candida, Aspergillus, Arxula adeninivorans, Candida boidinii, Hansenula polymorpha (Pichia angusta), Kluyveromyces lactis, Pichia pastoris, Saccharomyces cerevisiae* and *Yarrowia lipolytica*, to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira*, and *Laminaria japonica*, and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., Addgene.org, which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues. Each of these databases is incorporated by reference herein in its entirety for all purposes.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ one or more expression plasmids hosting 3 or more ORFs for convenience, but it may be preferred to insert operons or individual genes into the genome for stability reasons.

Still further improvements in yield can be made by removing competing pathways, such as those pathways for making e.g., acetate, formate, ethanol, and lactate, and it is already well known in the art how to reduce or knockout these pathways. See e.g., the inventors' prior patents.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250, and available through the NCBI website. The default parameters were used, except the filters were turned OFF.

As used herein, the expressions "cell", "cell line" and "cell culture" are used interchangeably and all such designations include progeny. Thus, the words "cells" and similar designations include the primary subject cell and cultures derived therefrom without regard for the number of generation. It is also understood that all progeny may not be precisely identical in DNA content, due to deliberate or inadvertent mutations that arise after engineering is concluded. Mutant progeny that have the same function or biological activity as screened for in the originally transformed cell are included. Where distinct designations are intended, it will be clear from the context. Furthermore, reference to "a" cell typically includes cultures of that cell, which is common usage in the art.

The terms "operably associated" or "operably linked," as used herein, refer to functionally coupled nucleic acid sequences.

As used herein, "engineered" means an organism being recombinantly modified to change its genetics in a particular way to achieve a particular result.

As used herein "recombinant" or "recombinant engineering" is relating to, derived from, or containing genetic material intentionally modified by the hand of man. In other words, the genetics were intentionally manipulated in some way.

By "metabolically modified" we refer to random mutagenesis and selective pressure to evolve an organism in a desired direction. Such procedures are often employed after a recombinant engineering step to further improve production of a desired product.

"Reduced activity" or "inactivation" or "down-regulated" is defined herein to be at least a 75% reduction in protein activity, as compared with an appropriate control species. Preferably, at least 80, 85, 90, 95% reduction in activity is attained, and in the most extreme embodiment, the activity is eliminated (100%). Proteins can be inactivated with inhibitors, by mutation, or by suppression of expression or translation, and the like.

The terms "disruption" as used herein, refer to cell strains in which the native gene or promoter is mutated, deleted, interrupted, or down regulated in such a way as to decrease the activity of the protein at least 90% over the wild type un-disrupted protein. A gene or protein can be completely (100%) reduced by "knockout" or removal of the entire genomic DNA sequence. A "knockout" or "null" mutant can be represented by the Δ symbol.

Use of a frame shift mutation, early stop codon, point mutations of critical residues, or deletions or insertions, and the like, can completely inactivate (100%) gene product by completely preventing transcription and/or translation of active protein.

"Overexpression" or "overexpressed" is defined herein to be at least 150% of protein activity as compared with an appropriate control species or as having detectable expression of a gene not normally present in that host. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, using highly active expression vectors, or upregulating the endogenous gene, and the like. An overexpressed gene can be represented by the $^+$ symbol, e.g., PYC$^+$. In contrast, "expression" refers to normal levels of activity or better.

Acid and base forms of a molecule are used interchangeably herein, thus use of butyrate is intended to and does include butanoic acid.

NAD$^+$ and NADH are used interchangeably herein, since the reactions involved convert one to the other. Likewise, NADP$^+$ and NADPH are used interchangeably.

An "NAPDH-dependent" enzyme relies on NADPH as a cofactor, whereas an "NADH-dependent" enzyme uses NADH. An "NA(P)DH-dependent" enzyme can use either.

"Growing" cells refers to exponentially dividing cell cultures.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
|---|---|
| AccA | acetyl-CoA carboxyltransferase alpha-subunit |
| ACP | acyl carrier protein |
| AcpP | Acyl carrier protein. |
| AlkH | Aldehyde dehydrogenase |
| AlkJ | alcohol dehydrogenase |
| AMP | Ampicillin resistance |
| ArmA | paired-termini to impart stability to antisense RNA |
| ArmB | paired-termini to impart stability to antisense RNA |
| AtoB | Acetyl-CoA acetyltransferase |
| CmR | chloramphenicol resistant gene |
| CoA | Coenzyme A |
| Crt | Crotonase-one example of a specific dehydratase, aka (aka 3-hydroxybutyryl-CoA dehydratase) |
| FA | Fatty acid |
| FabA | 3-hydroxydecanoyl-[acyl-carrier-protein] dehydratase |
| FabB | 3-oxoacyl-[ACP] synthase I |
| FabD | malonyl-CoA-[ACP] transacylase |
| FabG | 3-oxoacyl-[ACP] reductase |
| FabI | enoyl-[ACP] reductase |
| FabZ | 3-hydroxyacyl-[acyl-carrier-protein] dehydratase |
| FAS | Fatty Acid synthesis |
| FatB | fatty acyl-ACP thioesterases, see also TE |
| IPTG | Isopropyl β-D-1-thiogalactopyranoside |
| KASIII | beta-ketoacyl-[acyl-carrier-protein] synthase III |
| LacI | Lac operon repressor |
| M9 media | M9 minimal media, commercially available |
| PhaA | = β-ketothiolase |
| PhaB | acetoacetyl-CoA reductase |
| PrpE | Propionate--CoA ligase |
| TE | Thioesterase |
| Ter | trans-enoyl-CoA reductase |

BRIEF DESCRIPTION OF DRAWINGS

FIG. 20: Prior art KASIII-dependent FAS system present in many wild type bacteria.

DETAILED DESCRIPTION

Figure 1:
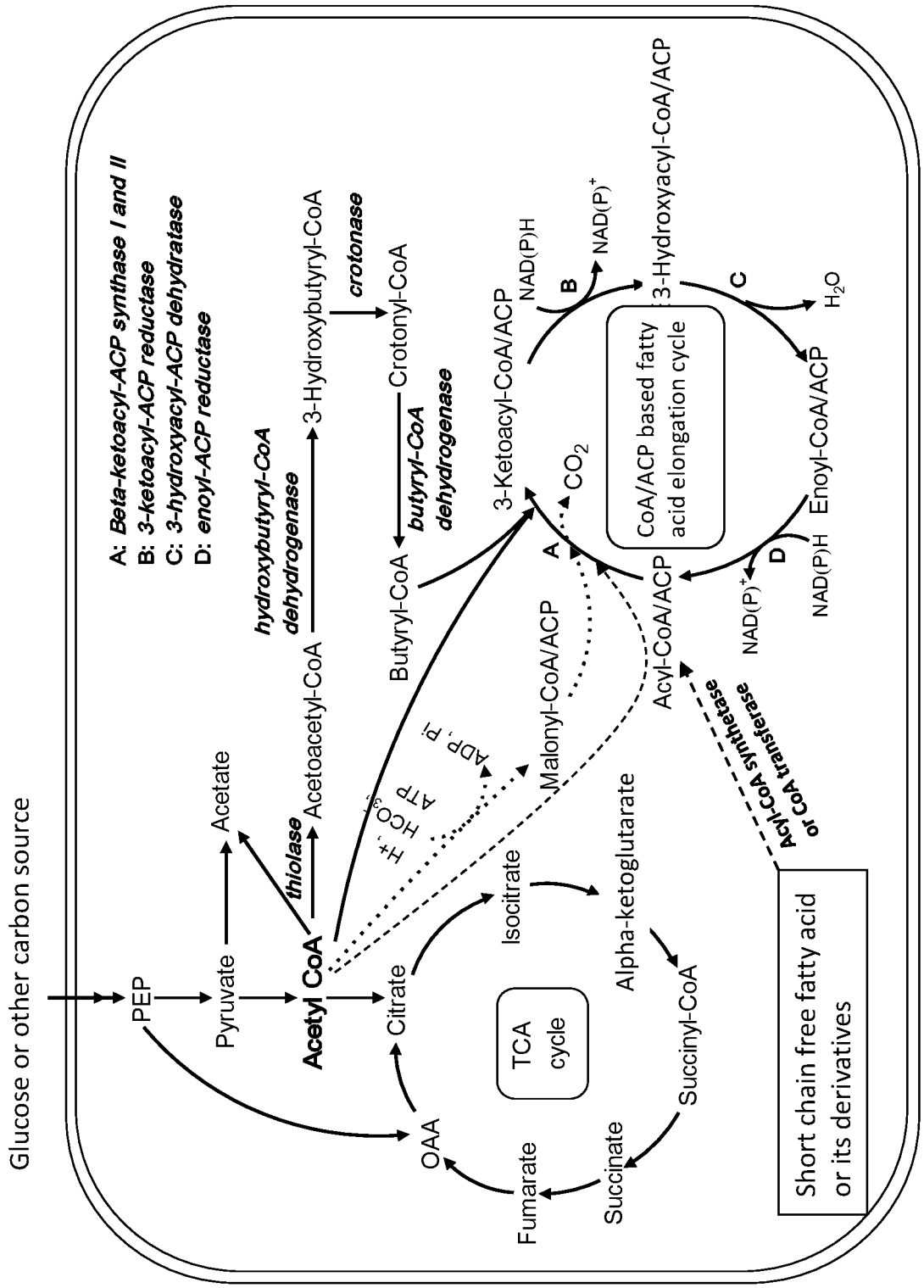
FIG. 1: Diagram showing the genetically engineered KASIII independent fatty acid biosynthetic pathway.

The invention provides a novel method of making fatty acids and various derivatives thereof that is KASIII-independent, thus avoiding the limiting substrate specificity of this initiating enzyme and allowing many more substrates to enter the FAS pathway and thus produced a wide variety of products.

The invention takes advantage of the remaining promiscuous enzymes of the fatty acid synthesis system (except for the initialization step involving the enzyme β-ketoacyl-acyl carrier protein synthase III, or also known as β-ketoacyl-ACP synthase III, 3-oxoacyl-ACP synthase III, KASIII, which is highly substrate specific). If desired, any of these genes can be overexpressed, but wild type levels may be sufficient for many purposes.

The enzymes involved in the fatty acid elongation cycle (3-ketoacyl-ACP synthetase, 3-ketoacyl-ACP reductase, 3-hydroxyacyl ACP dehydrase, enoyl-ACP reductase) have broad substrate specificity. The same set of enzymes can accept a wide range of carbon chain length as a substrate, making the system very versatile in making products of various chain lengths. The same set of enzymes can also accept a wide range of molecules that are derivatives of the usual substrates (such as with those with branched chain, containing additional other functional groups, for example hydroxy group, amine group, halogen, and the like) making the system very versatile in making a set of highly diversified products.

This invention thus allows us to bypass the gate-keeping step, a reaction catalyzed by the β-ketoacyl-acyl carrier protein synthase III aka KASIII, by supplying the cells in vivo with a longer Co-A substrate (more than two carbon), such as butyryl-CoA, or a derivative of the usual substrate, such as an omega functionalized CoA primer, so that the cells can use the existing fatty acid synthesis system to make functionalized and other unusual fatty acids.

In addition, this invention of synthesizing fatty acids and fatty acid derivatives does not rely on, but can co-exist with, the ACP-based fatty acid elongation cycle. Alternatively, the native KASIII can be down regulated to reduce competition. Knock-out mutants can also be used. Although ΔKASIII mutants grow slowly, they can be grown if supplemented. In fact, we have already created the mutant strain HWK201 (with a KASIII knockout) for use in the invention.

The ≥2 C, ≥3 C, ≥4 C etc. primer or starter molecule can be supplied to the cell, e.g., in the medium, or the cell can be provided with the enzymes needed to make this primer. An example of providing butyryl-CoA from acetyl-CoA is provided.

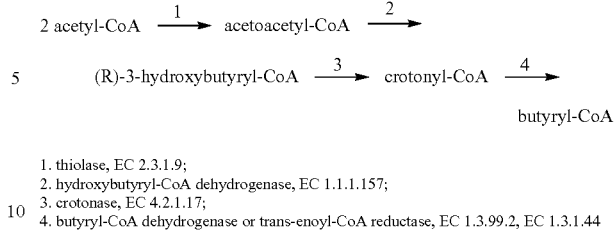

1. thiolase, EC 2.3.1.9;
2. hydroxybutyryl-CoA dehydrogenase, EC 1.1.1.157;
3. crotonase, EC 4.2.1.17;
4. butyryl-CoA dehydrogenase or trans-enoyl-CoA reductase, EC 1.3.99.2, EC 1.3.1.44

Below is a table showing an example of steps and enzymes involved for the conversion of acetyl-CoA to butyryl-CoA.

| Examples of typical enzymes for converting acetyl-CoA to various intermediates | | |
|---|---|---|
| 1 EC 2.3.1.9, thiolase | C. acetobutylicum | thlA |
| | E. coli | atoB |
| | R. eutropha | phaA |
| 2 EC 1.1.1.157 hydroxybutyryl-CoA dehydrogenase | C. acetobutylicum | hbd |
| | R. eutropha | P06-PaaH1 |
| | R. eutropha | phaB |
| 3 EC 4.2.1.17 crotonase or enoyl-CoA hydratase | C. acetobutylicum | crt |
| 4 EC 1.3.99.2 butyryl-CoA dehydrogenase EC 1.3.1.44 | C. acetobutylicum | bcd & etfAB |
| | T. denticola, C.a. | ter |

| Strain | Gene | Exmplified gene in this patent | GenBank Accession or Gene ID | Protein_ID |
|---|---|---|---|---|
| R. eutropha | phaA | re_phaA | 4249783 | CAJ92573.1 |
| T. eutropha | phaB | re phaB | 4249784 | CAJ92574.1 |
| T. denticola | ter | td_ter | 2741560 | AAS11092.1 |
| C. acetobutylicum | crt | ca_crt | 1118895 | AAA95967.1 |
| E. coli | atoB | ec_atoB | 946727 | AAC75284.1 |
| E. coli | fabG | ec_fabG | 945645 | AAC74177.1 |
| E. coli | fabI | ec_fabI | 945870 | AAC74370.1 |
| E. coli | fabZ | ec_fabZ | 944888 | AAC73291.1 |
| E. coli | fabD | ec_fabD | 945766 | AAC74176.1 |
| E. coli | fabH | ec_fabH | 946003 | AAC74175.1 |
| E. coli | fabA | ec_fabA | 945568 | AAC74040.1 |
| E. coli | fabB | ec_fabB | 946799 | AAC75383.1 |
| E. coli | acpP | ec_acpP | 944805 | AAC74178.1 |
| E. coli | accA | ec_accA | 944895 | AAC73296.1 |
| S. enterica | PrpE | se_prpE | 1251890 | AFD57404.1 |
| California Bay Tree | UcfatB | TE12 | M94159.1 | |
| P. putida P1 | alkJ | | AJ233397 | CAB51051.1 |
| P. putida P1 | alkH | | AJ233397 | CAB51050.1 |

The above genes are exemplary only, and many of the accession numbers are linked to homologs from other species that can be used herein. Further, the use of EC numbers will identify even more homologs.

Different carbon chain length fatty acids and fatty acid derivatives using the KASIII-independent FAS cycle can be produced by using various acyl-ACP thioesterases (TE) with appropriate substrate specificity, which are expressed in the cell or preferably overexpressed. Examples of the TE enzymes are: *Umbellularia californica* TE (GenBank #AAC49001), *Cinnamomum camphora* TE (GenBank #Q39473), *Umbellularia californica* TE (GenBank #Q41635), *Myristica fragrans* TE (GenBank #AAB71729), *Myristica fragrans* TE (GenBank #AAB71730), *Elaeis guineensis* TE (GenBank #ABD83939), *Elaeis guineensis* TE (GenBank #AAD42220), *Populus tomentosa* TE (GenBank #ABC47311), *Arabidopsis thaliana* TE (GenBank #NP-172327), *Arabidopsis thaliana* TE (GenBank #CAA85387), *Arabidopsis thaliana* TE (GenBank #CAA85388), *Gossypium hirsutum* TE (GenBank #Q9SQI3), *Cuphea lanceolata* TE (GenBank #CAA54060), *Cuphea hookeriana* TE (GenBank #AAC72882), *Cuphea calophylla* subsp. *mesostemon* TE (GenBank #ABB71581),

*Cuphea lanceolata* TE (GenBank #CAC19933), *Elaeis guineensis* TE (GenBank #AAL15645), *Cuphea hookeriana* TE (GenBank #Q39513), *Gossypium hirsutum* TE (GenBank #AAD01982), *Vitis vinifera* TE (GenBank #CAN81819), *Garcinia mangostana* TE (GenBank #AAB51525), *Brassica juncea* TE (GenBank #ABI18986), *Madhuca longifolia* TE (GenBank #AAX51637), *Brassica napus* TE (GenBank #ABH11710), *Oryza sativa* (indica cultivar-group) TE (GenBank #EAY86877), *Oryza sativa* (*japonica* cultivar-group) TE (GenBank #NP-001068400), *Oryza sativa* (indica cultivar-group) TE (GenBank #EAY99617), and *Cuphea hookeriana* TE (GenBank #AAC49269), *Escherichia coli* TE II (ECK0446). Hundreds of TE genes have been clotted and characterized, and can be used herein. See e.g. Jing 2011.

By "long chain" acyl-ACP thioesterase, what is meant herein, is that the TE produces a preponderance of long chain (>C12) fatty acids. Preferably, such TE produces more than 50%, >60%, or >70% of a fatty acid >C12.

By "short chain" acyl-ACP thioesterase, what is meant herein, is that the TE produces a preponderance of short chain (≤C12) fatty acids. Preferably, such TE produces more than 50%, >60%, or >70% of a fatty acid ≤C12.

The disclosed method is capable of producing C4-C20 or C6-C18 hydroxy fatty acids, amino fatty acids, halogenated fatty acids, branched fatty acids, unsaturated fatty acids, or a ω-hydroxy fatty acids, bifunctional fatty acids, or derivatives thereof from the engineered pathway.

Vectors

Plasmid pHWABTC was designed, as an example, to overexpress four genes necessary for the conversion of acetyl-CoA to butyryl-CoA, thus bypassing the normal KASIII entry point. The enzymes exemplified herein are illustrative only, and any enzyme with the same CE number can be employed, and tested to confirm adequate activity.

Figure 2:
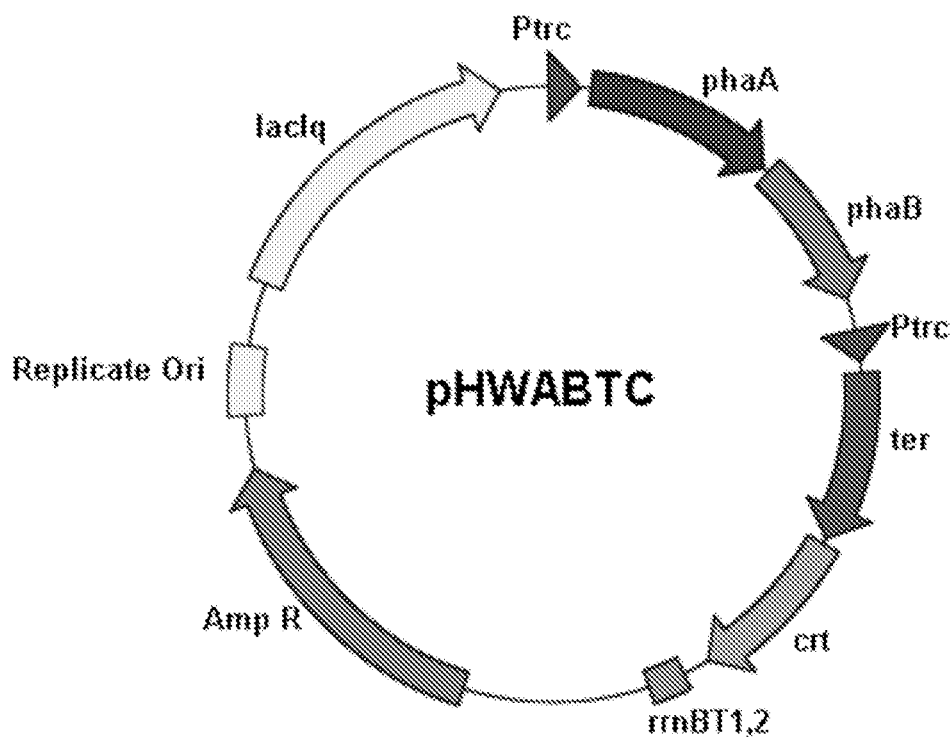
FIG. 2: Schematic diagram of pHWABTC. Abbreviations: phaA gene from *Ralstonia eutropha* H16; phaB gene from *R. eutropha* H16; ter gene from *Treponema denticola*; crt gene from *Clostridium acetobutylicum*; pTrc, trc promoter; lad, lac operon repressor; Amp, ampicillin resistant gene; pBR322 origin, origin of replication of plasmid pBR322, rrnBT1,2, transcriptional terminator of rrnB.

A schematic diagram of pHWABTC is shown in FIG. 2. The 1499 bp of gene sequence including Trc promoter and ter gene encoded the trans-enoyl-coenzyme A reductase from *Treponema denticola* was synthesized and cloned into the vector pTrc99a-phaAB. The plasmid was named pHWABT. Then 1091 bp of gene sequence including RBS and crt gene encoded the crotonase from *Clostridium acetobutylicum* was synthesized and cloned into the vector pHWABT to make pHWABTC. The newly constructed pHWABTC expressed the β-ketothiolase from *Ralstonia eutropha* H16, acetoacetyl-CoA reductase from *Ralstonia eutropha* H16, trans-enoyl-coenzyme A reductase from *T. denticola*, and crotonase (aka 3-hydroxybutyryl-CoA dehydratase) from *C. acetobutylicum*.

Figure 3:
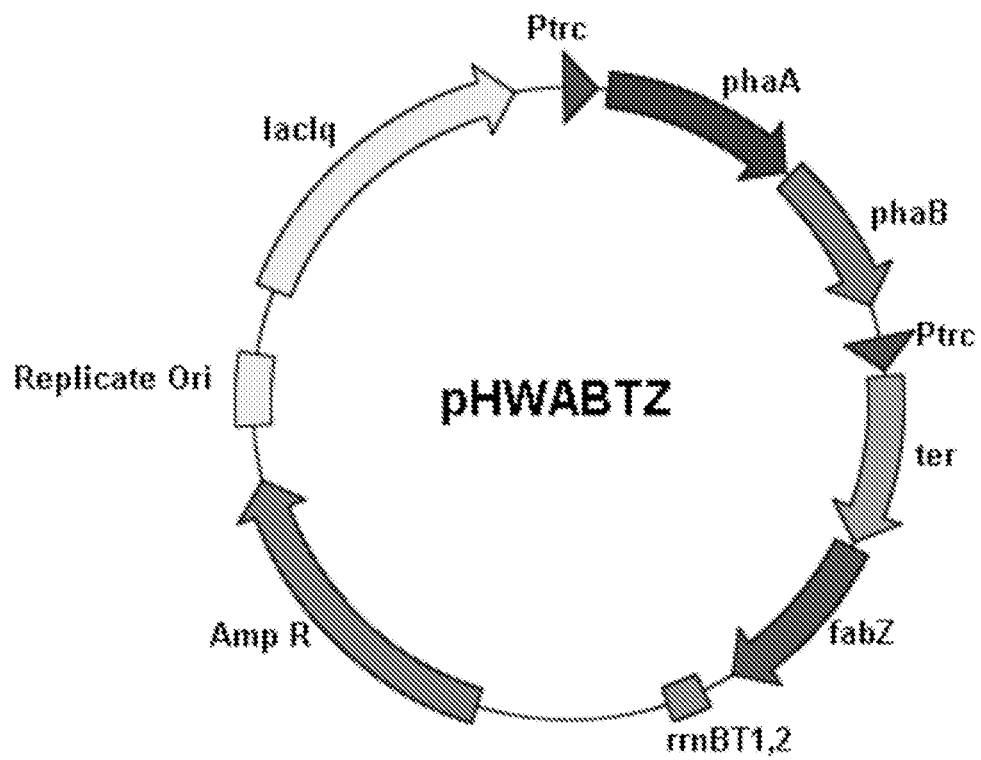
FIG. 3: Schematic diagram of pHWABTZ. Abbreviations: phaA gene from *R. eutropha* H16; phaB gene from *R. eutropha* H16; ter gene from *T. denticola*; fabZ gene from *E. coli*; pTrc, trc promoter; lad, lac operon repressor; Amp, ampicillin resistant gene; pBR322 origin, origin of replication of plasmid pBR322, rrnBT1,2, transcriptional terminator of rrnB.

The schematic diagram of pHWABTZ is shown in FIG. 3. The 1499 bp of gene sequence including Trc promoter and ter gene encoding the trans-enoyl-coenzyme A reductase from *Treponema denticola* was synthesized and cloned into the vector pTrc99a-phaAB to make pHWABT. The 456 bp fabZ of *E. coli* plus RBS was amplified from the genome of MG1655. The primers used in this experiment are listed in Table 1.

The PCR fragments were digested by restriction enzymes, BamHI and XbaI, and ligated to plasmid pHWABT, also digested with BamHI and XbaI, to make pHWABTZ. The newly constructed pHWABTZ expressed the β-ketothiolase from *Ralstonia eutropha* H16, acetoacetyl-CoA reductase from *Ralstonia eutropha* H16, trans-enoyl-coenzyme A reductase from *Treponema denticola*, and 3-hydroxyacyl-ACP dehydrase from *E. coli*.

TABLE 1

The primers used in this experiment.

| Primers | Sequences |
| --- | --- |
| pHWABT-fabZ-F | GCGCGggatccGAGGAGGACAGCTatgactactaa cactcatac |
| pHWABT-fabZ-R | gcgccTCTAGAtcaggcctcccggctacgag |

Figure 4:
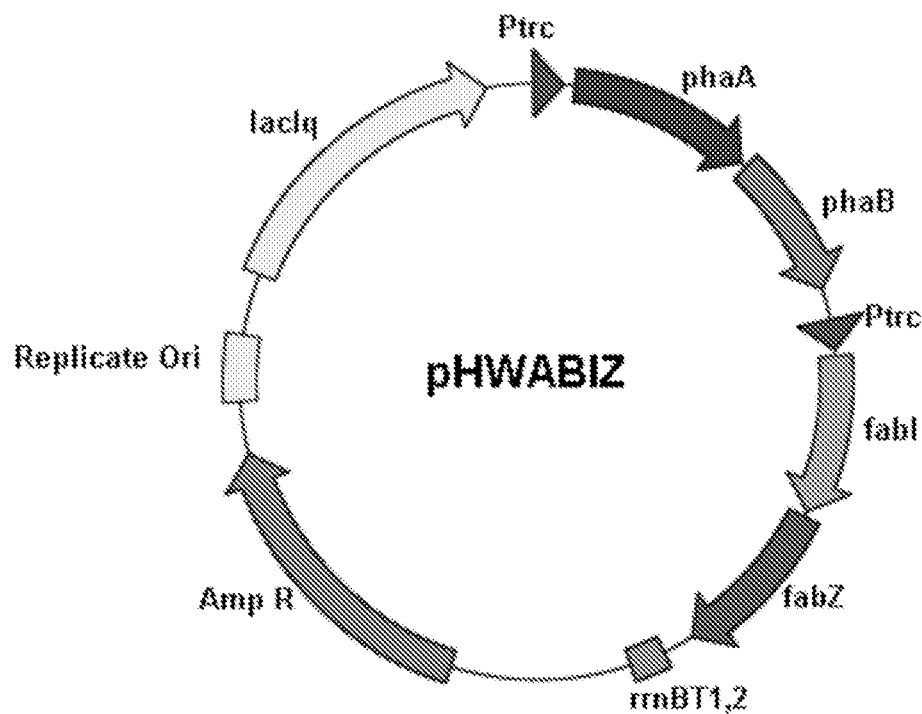
FIG. 4: Schematic diagram of pHWABIZ. Abbreviations: phaA gene from *R. eutropha* H16; phaB gene from *R. eutropha* H16; fabI gene from *E. coli*; fabZ gene from *E. coli*; pTrc, trc promoter; lad, lac operon repressor; Amp, ampicillin resistant gene; pBR322 origin, origin of replication of plasmid pBR322, rrnBT1,2, transcriptional terminator of rrnB.

The schematic diagram of pHWABIZ is shown in FIG. 4. The gene ter from *Treponema denticola* in the vector pHWABTZ was replaced by the 789 bp fabI gene encoding the enoyl-ACP reductase from *E. coli*. The in fusion method was applied in this construction. The primers used in this experiment are listed in Table 2. The plasmid was named pHWABIZ and expressed the β-ketothiolase from *Ralstonia eutropha* H16, acetoacetyl-CoA reductase from *Ralstonia eutropha* H16, enoyl-ACP reductase from *E. coli*, and 3-hydroxyacyl-ACP dehydrase from *E. coli*.

TABLE 2

The primers used in this experiment.

| Primers | Sequences |
| --- | --- |
| pHWABIZ-P-R | atggtctgtttcctgtgtgaaa |
| pHWABIZ-P-F | ggatccgaggaggacagctat |
| pHWABIZ-I-F | aatttcacacaggaaacagaccatgggttttctttcc ggtaa |
| pHWABIZ-I-R | atagctgtcctcctcggatccttatttcagttcgagt tcg |

Figure 5:
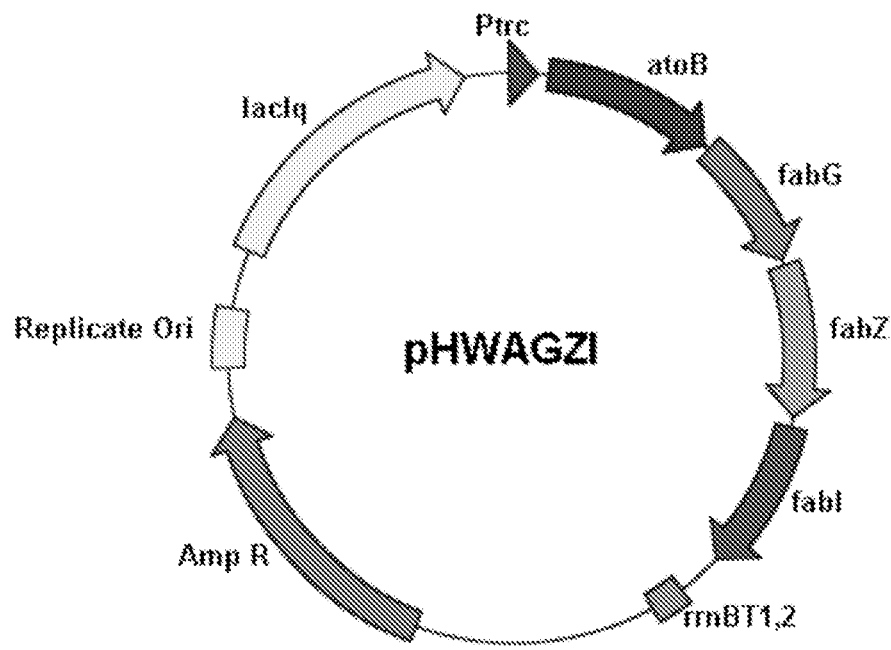
FIG. 5: Schematic diagram of pHWAGZI. Abbreviations: atoB gene from *E. coli*; fabG gene from *E. coli*; fabZ gene from *E. coli*; fabI gene from *E. coli*; pTrc, trc promoter; lad, lac operon repressor; Amp, ampicillin resistant gene; pBR322 origin, origin of replication of plasmid pBR322, rrnBT1,2, transcriptional terminator of rrnB.

The schematic of pHWAGZI is shown in FIG. 5. The 1185 bp atoB encoding acetyl-CoA acetyltransferase of *E. coli* was amplified from the genome of MG1655. The PCR fragments were digested by restriction enzymes, SacI and BamHI, and ligated to plasmid pTUM3-mch, which was also digested with SacI and BamHI. The plasmid was named pTrc-atoB-TUM3-mch. The 748 bp of fabG, encoded β-ketoacyl-ACP reductase of *E. coli*, plus RBS was amplified from the genome of MG1655.

The PCR fragments were digested by restriction enzymes, BamHI and XbaI, and ligated to plasmid pTrc-atoB-TUM3-mch, which was also digested with BamHI and XbaI to make pHWAGM. The fragments of pTrc-atoB-fabG were amplified from pHWAGM. The fabI gene encoding the enoyl-ACP reductase plus RBS and the fabZ gene encoding 3-hydroxyacyl-ACP dehydrase of *E. coli* plus RBS from *E. coli* were amplified from the genome of MG1655.

The three fragments were assembled by the kit of GENEART® Seamless Cloning and Assembly Kit to make pHWAGZI. The primers used in this experiment are listed in Table 3. The newly constructed pHWAGZI expressed the acetyl-CoA acetyltransferase, β-ketoacyl-ACP reductase, 3-hydroxyacyl-ACP dehydrase, and enoyl-ACP reductase from *E. coli*.

TABLE 3

The primers used in this experiment.

| Primers | Sequences |
| --- | --- |
| pHWAGM-AtoB-F | GCGCcGAGCTCatgaaaaattgtgtcatcgt |
| pHWAGM-AtoB-R | gcgccggatccaattcaaccgttcaatca |

TABLE 3-continued

The primers used in this experiment.

| Primers | Sequences |
|---|---|
| pHWAGM-fabG-F | GCGCGggatccGAGGAGGACAGCTatgaattttgaaggaaaaatcgc |
| pHWAGM-fabG-R | gcgccTCTAGAtcagaccatgtacatcccgc |
| pWHAG-F | aagcttggctgttttggcggatga |
| pWHAG-R | tctagatcagaccatgtacatccc |
| pWHAG-fabZ-F | gcgggatgtacatggtctgatctagaagatctgtcgacactagtGAGGAGGACAGCTatgactactaacactcatac |
| pWHAG-fabZ-R | GAATTCTCAGGCCTCCCGGCTACG |
| pWHAG-fabI-F | gaggcctgagaattcGAGGAGGACAGCTatgggtttctcttccggtaagc |
| pWHAG-fabI-R | atcttctctcatccgccaaaacagcc |

Figure 6:
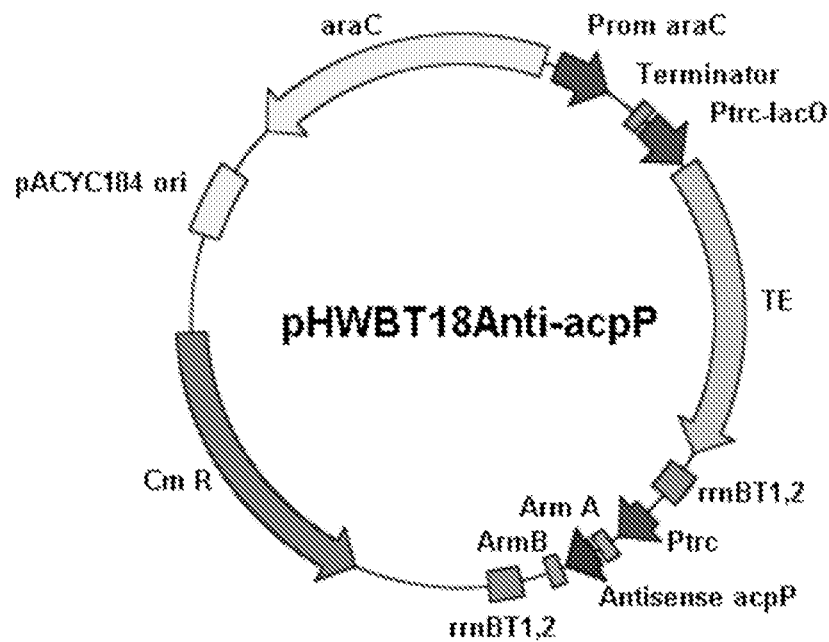
FIG. 6: Schematic diagram of pHWBT18Anti-acpP. Abbreviations: TE gene from *R. communis*; Antisense acpP gene, antisense sequence of acpP gene from *E. coli*; ArmA and ArmB, forming paired-termini to impart stability to antisense RNA after expression; pTrc-lacO, trc promoter without lacO binding site; pTrc, trc promoter; lad, lac operon repressor; CmR, chloramphenicol resistant gene; pACYC184 ori, origin of replication of plasmid pACYC184, rrnBT1,2, transcriptional terminator of rrnB.

The schematic diagram of pHWBT18Anti-acpP is shown in FIG. 6. There four steps for constructing this plasmid. Firstly, the SacI site of pBAD33 was removed. The method of in fusion was used in this step. The plasmid PCR fragments without SacI site ligated by themselves to form the plasmid pBAD33-SacI⁻. Secondly, the gene fragment of Trc promoter without lacO binding site and the TE gene from *R. communis* was amplified from the plasmid pWL1T.

The PCR fragments were digested by restriction enzymes, KpnI and XbaI, and ligated to plasmid pBAD33-SacI⁻, which was also digested with KpnI and XbaI. The plasmid was named pBAD33-SacI⁻-T18.

Thirdly, the fragment consisting of terminator, Trc promoter and antisense RNA with paired-termini was amplified from pBSK-antisense. The PCR fragments were digested by restriction enzymes, SalI and SphI, and ligated to plasmid pBAD33-SacI⁻-T18, also digested with SalI and SphI. The plasmid was named pHWBT18Anti.

Fourthly, the 127 bp reverse sequence of acpP of *E. coli* including RBS and some of its front part, from −43 to 84, was amplified from the genome of MG1655. The PCR fragments were digested by restriction enzymes, SacI and XhoI, and ligated to plasmid pHWBT18Anti, also digested with SacI and XhoI. The plasmid was named pHWBT18Anti-acpP. The primers used in this experiment are listed in Table 4.

TABLE 4

The primers used in this experiment.

| Primers | Sequences |
|---|---|
| pBAD-SacI-F | ggctcggtacccggggatcctctagagtcgac |
| pBAD-SacI-R | cgctcggtaccgaattcgctagcccaaaaaacgggtat |
| Trc-lacO-18-F | GCGCGggtaccgcgcaacgcaattaatgtgagttagcg |
| Trc-lacO-18-R | GCGGCtctagattaggcgctttcaaccggaatttg |
| Anti sense-F | GCGCGgtcgacggctgttttggcggatgagagaagattttc |
| Anti sense-R | tcgaggatatccccgcatgcaggaggaattaaccatgca |

TABLE 4-continued

The primers used in this experiment.

| Primers | Sequences |
|---|---|
| Anti-acpP-F | GCGCGgagctcaagaagcattgttggtaact |
| Anti-acpP-R | atcttctctcatccgccaaaacagcc |

Figure 7:
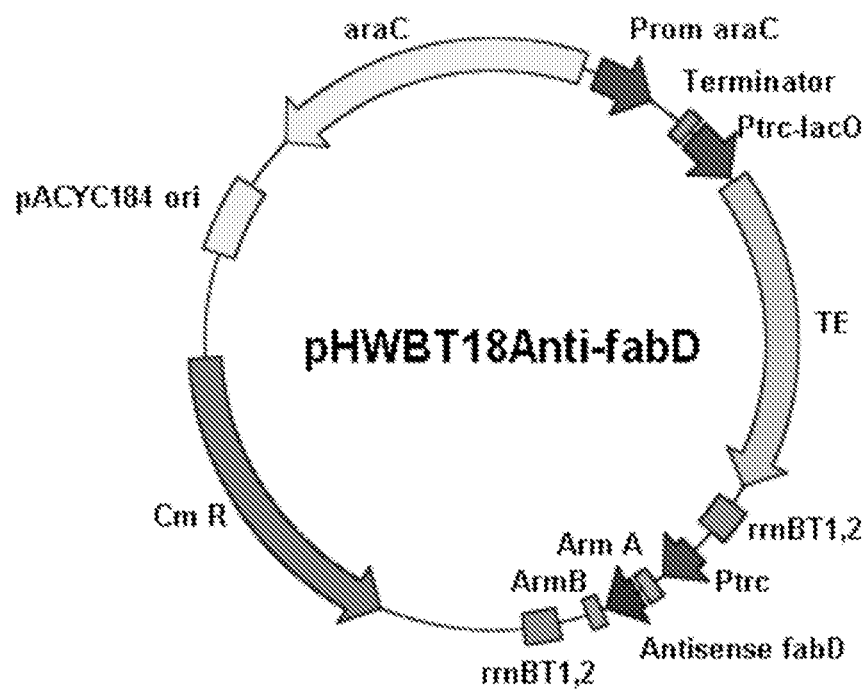
FIG. 7: Schematic diagram of pHWBT18Anti-fabD. Abbreviations: TE gene from *R. communis*; Antisense fabD gene, antisense sequence of fabD gene from *E. coli*; ArmA and ArmB, forming paired-termini to impart stability to antisense RNA after expression; pTrc-lacO trc promoter without lacO binding site; pTrc, trc promoter; lad, lac operon repressor; Amp, ampicillin resistant gene; pACYC184 ori, origin of replication of plasmid pACYC184, rrnBT1,2, transcriptional terminator of rrnB.

The schematic diagram of pHWBT18Anti-fabD is shown in FIG. 7. The 151 bp reverse sequence of fabD of *E. coli* including RBS and some of its front portion, from −15 to 136, was amplified from the genome of MG1655. The PCR fragments were digested by restriction enzymes, SacI and XhoI, and ligated to plasmid pHWBT18Anti, also cut with SacI and XhoI. The plasmid was named pHWBT18Anti-fabD. The primers used in this experiment are listed in Table 5.

TABLE 5

The primers used in this experiment.

| Primers | Sequences |
|---|---|
| Anti-fabD-F | GCGCGgagctccccacaggtcgtagcccagc |
| Anti-fabD-R | ccGgcctcgaggataaggattaaaacatgac |

Fat Production

A single colony of strain HWK201(pWL4T), HWK201 (pTrc99a, pWL4T) or HWK201(pHWABTZ, pWL4T) was inoculated into 5 ml of Luria-Bertani (LB) and incubated in an orbital shaker operated at 250 rpm at 37° C. overnight. The preculture was inoculated into a flask containing 50 mL of the culture medium with 1% (v/v) inoculum. The culture medium contained: tryptone 10 g/L, yeast extract 5 g/L, NaCl 5 g/L, glycerol 15 g/L, ampicillin 100 µg/L, pH 7.5. Different concentrations of IPTG were investigated. Shake flask experiment was performed at 30° C. with shaking at 250 rpm for 72 h. The samples were extracted using the method developed in our lab (Zhang et al., 2011). The fatty acid concentration was quantified by a GC-FID system (Table 6). These conditions are generally employed throughout, with modification as noted.

TABLE 6

Concentration of fatty acid production of strains HWK201 (pWL4T), HWK201 (pTrc99a, pWL4T), and HWK201 (pHWABTZ, pWL4T)

| Strain | Relevant genotype | IPTG (mM) | Concentration of total fatty acid (mg/L) | | |
|---|---|---|---|---|---|
| | | | 24 h | 48 h | 72 h |
| HWK201 (pWL4T) | ΔfadD, ΔfabH, rc_TE⁺ | — | Not determined | 52 | 61 |
| HWK201 (pTrc99a, pWL4T) | ΔfadD, ΔfabH, rc_TE⁺ | — | Not determined | 48 | 60 |

TABLE 6-continued

Concentration of fatty acid production
of strains HWK201 (pWL4T), HWK201 (pTrc99a,
pWL4T), and HWK201 (pHWABTZ, pWL4T)

| Strain | Relevant genotype | IPTG (mM) | Concentration of total fatty acid (mg/L) | | |
|---|---|---|---|---|---|
| | | | 24 h | 48 h | 72 h |
| HWK201 (pHWABTZ, pWL4T) | ΔfadD, ΔfabH, re_PhaA+, re_PhaB+, td_TER+, ec_FabZ+, rc_TE+ | 0.00 | 46.15 | 62 | 66 |
| | | 0.05 | 63.31 | 201 | 213 |
| | | 0.10 | 35.67 | 127 | 125 |
| | | 0.20 | 32.23 | 120 | 123 |
| | | 0.50 | 31.08 | 125 | 122 |
| | | 1.00 | 20.25 | 106 | 116 | re_PhaA+: overexpression of β-ketothiolase from *Ralstonia eutropha* H16 in pTrc99a
re_PhaB+: overexpression of acetoacetyl-CoA reductase from *Ralstonia eutropha* H16 in pTrc99a
td_TER+: overexpression of trans-enoyl-coenzyme A reductase from *Treponema denticola* in pTrc99a
ec_FabZ+: overexpression of 3-hydroxyacyl-ACP dehydrase from *E. coli* in pTrc99a
rc_TE+: overexpression of acyl-ACP thioesterase from *Ricinus communis* under the TUM3 promoter in pBAD33
ΔfadD: deactivation of acyl-CoA synthetase
ΔfabH: deactivation of β-ketoacyl-acyl carrier protein synthase III The host strain HWK201 is an *E. coli* strain with a deactivated KASIII—which is the enzyme involved in the initialization step of the fatty acid synthesis cycle. The strains HWK201 (pWL4T) and HWK201 (pTrc99a, pWL4T) served as the control. Both strains lack the four genes re phaA, re phaB, td ter, ec fabZ that encode for enzymes to convert acetyl-CoA to butyryl-CoA, and which together function as the added primer synthesis pathway. Both strains produced about 60 mg/L of fatty acid at 72 hrs. This low level of fatty acid production is due to the deactivation of KASIII, which encodes the enzyme involved in the initialization step of the fatty acid synthesis cycle.

However, upon induction of the plasmid, pHWABTZ, carrying the genes re phaA, re phaB, td ter, ec fabZ, which encode for enzymes to convert acetyl-CoA to butyryl-CoA, fatty acid production is significantly increased (Table 6). These results support the claim that the FAS cycle can be activated in KASIII deficient strains if the cells are supplied with butyryl-CoA. Although this is not a functionalized primer molecule, this experiment proves that it is possible to bypass KASIII and make fats using the remaining enzymes.

A second experiment was performed to further confirm the functionality of the invention, but using a different enzyme set. A single colony of strain HWK201 (pHWABTC, pWL4T) was inoculated into 5 ml of LB and treated as above. The fatty acid concentration was quantified by a GC-FID system (Table 7).

In this study the 3-hydroxyacyl-ACP dehydrase from *E. coli* (ec FabZ) was substituted by a crotonase from *Clostridium acetobutylicum* (Ca CRT) in order to provide yet another example of making an initiating primer in the cell, thus bypassing the KASIII starting enzyme.

Similar to the above experiment, upon induction of the plasmid, pHWABTC, carrying the primer pathway genes re phaA, re phaB, td ter, ca crt, fatty acid production is significantly increased (Table 7). Again, the results support the claim that the FAS cycle can be activated in KASIII deficient strains if the cells are supplied with butyryl-CoA. That is, KASIII deficient strains cell can use butyryl-CoA as the priming molecule for the FAS cycle, bypassing KASIII.

TABLE 7

Concentration of fatty acid production
of strain HWK201 (pHWABTC, pWL4T)

| Strain | Relevant genotype | IPTG (mM) | Concentration of total fatty acid (mg/L) | | |
|---|---|---|---|---|---|
| | | | 24 h | 48 h | 72 h |
| HWK201 (pHWABTC, pWL4T) | ΔfadD, ΔfabH, re_PhaA+, re_PhaB+, td_TER+, ca_CRT+, rc_TE+ | 0 | 41.43 | 41.26 | 45.53 |
| | | 0.05 | 77.46 | 102.19 | 94.38 |
| | | 0.1 | 77.19 | 100.06 | 100.31 |
| | | 0.2 | 31.53 | 102.14 | 104.01 |
| | | 0.5 | 13.48 | 55.99 | 62.74 |
| | | 1 | 14.09 | 61.35 | 70.10 | re_PhaA+: overexpression of β-ketothiolase from *Ralstonia eutropha* H16 in pTrc99a
re_PhaB+: overexpression of acetoacetyl-CoA reductase from *Ralstonia eutropha* H16 in pTrc99a
td_TER+: overexpression of trans-enoyl-coenzyme A reductase from *Treponema denticola* in pTrc99a
ca_CRT+: overexpression of crotonase from *Clostridium acetobutylicum* in pTrc99a
rc_TE+: overexpression of acyl-ACP thioesterase from *Ricinus communis* under the TUM3 promoter in pBAD33
ΔfadD: deactivation of acyl-CoA synthetase
ΔfabH: deactivation of β-ketoacyl-acyl carrier protein synthase III fabD Antisense In order to prove that the FAS pathway was truly KASIII independent, we turned off the fadD gene encoding malonyl-CoA-acyl carrier protein transacylase using antisense. This is expected to slow cell growth significantly. In the following experiment, the cells were then rescued by adding back in a primer pathway that bypasses the usual KASIII entry point.

Figure 10:
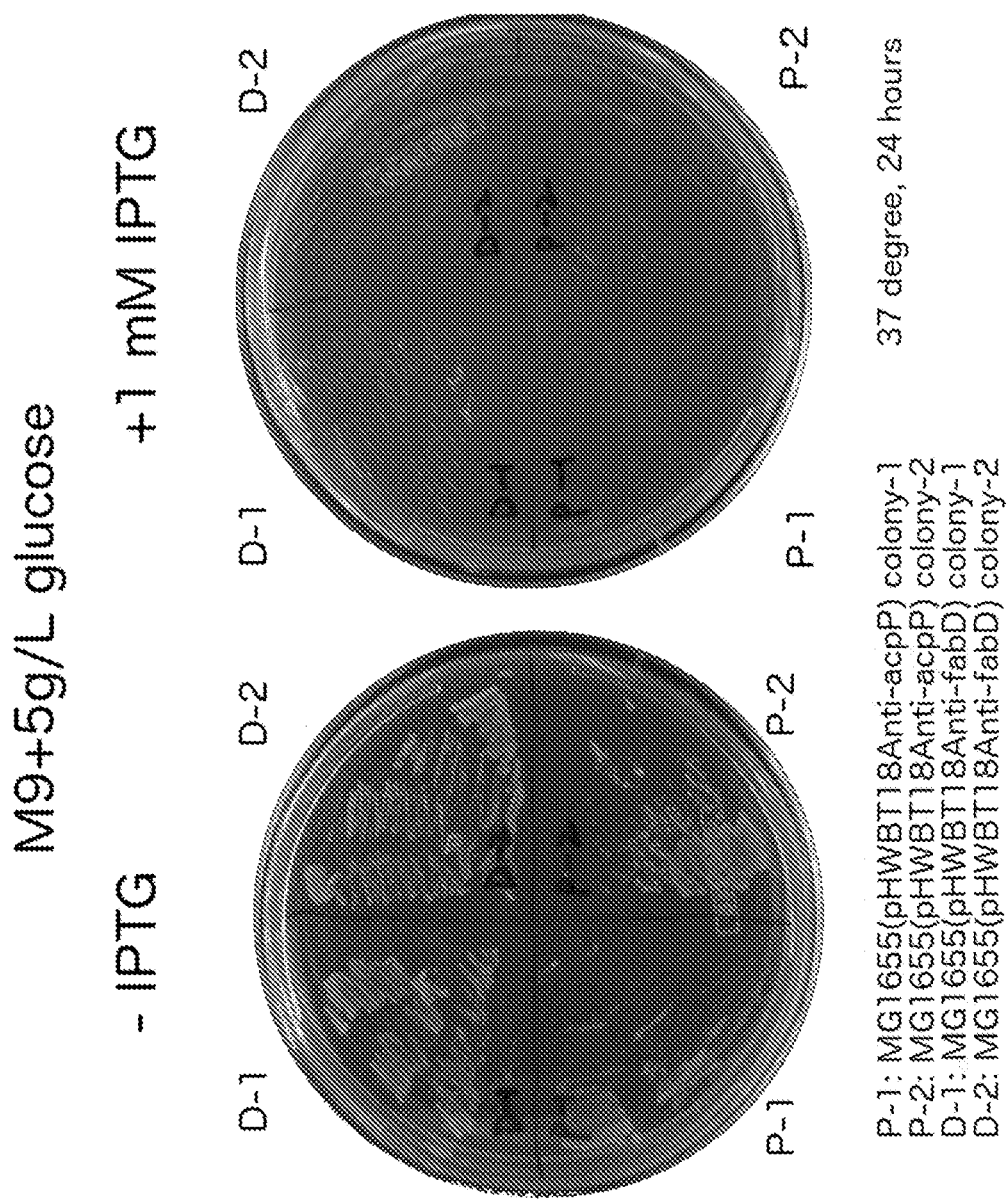
FIG. 10: Photograph showing colony formation on the IPTG free M9 plus glucose plate (10a) and on the 1 mM IPTG M9 plus glucose plate (10b).

The strain MG1655 (pHWBT18Anti-fadD), which carries the antisense-fabD gene under the control of an inducible trc promoter system, was chosen for this experiment. Two single colonies of the strain MG1655 (pHWBT18Anti-fabD) were selected from a plate containing freshly transformed cells. These selected colonies were streaked onto two M9 supplemented with glucose agar plates, one containing 1 mM IPTG and the other without. Both plates were incubated in a 37° C. incubator and the results are shown in FIG. 10.

Malonyl-CoA-ACP transacylase (FabD) catalyzes the conversion of malonyl-CoA to malonyl-ACP, one of the early steps of fatty acid biosynthesis and is deemed to be essential for cell growth. The strain MG1655 (pHWBT18Anti-fadD) carries the antisense-fabD gene under the control of an inducible trc promoter system showed normal growth on normal M9-glucose plate (top half, FIG. 10, 10a) and much reduced growth on IPTG supplemented M9-glucose plate (top half, FIG. 10, 10b). These results indicate that the anti-fabD antisense is functional in suppressing cell growth and induction in the presence of IPTG prevents the formation of malonyl-ACP from malonyl-CoA and thus leading to much reduced cell growth.

This second experiment demonstrates fatty acid synthesis can be re-activated by providing butyryl-CoA, a four-carbon Co-A based substrate, independent of KASIII and/or malonyl ACP.

The strain MG1655 (pHWBT18Anti-fabD, pHWABTZ) carries an anti-sense fabD gene, plus four genes which encode the enzymes for the formation of butyryl-CoA from acetyl-CoA: β-ketothiolase from *Ralstonia eutropha* H16, acetoacetyl-CoA reductase from *Ralstonia eutropha* H16, trans-enoyl-coenzyme A reductase from *Treponema denticola*, and 3-hydroxyacyl-ACP dehydrase from *E. coli*.

A single colony was selected from a plate containing freshly transformed cells. The selected colony was streaked onto two M9 supplemented with glucose agar plates, one containing 1 mM IPTG and the other without. Both plates were incubated in a 37° C. incubator and the results are shown in FIG. 11.

Figure 11:
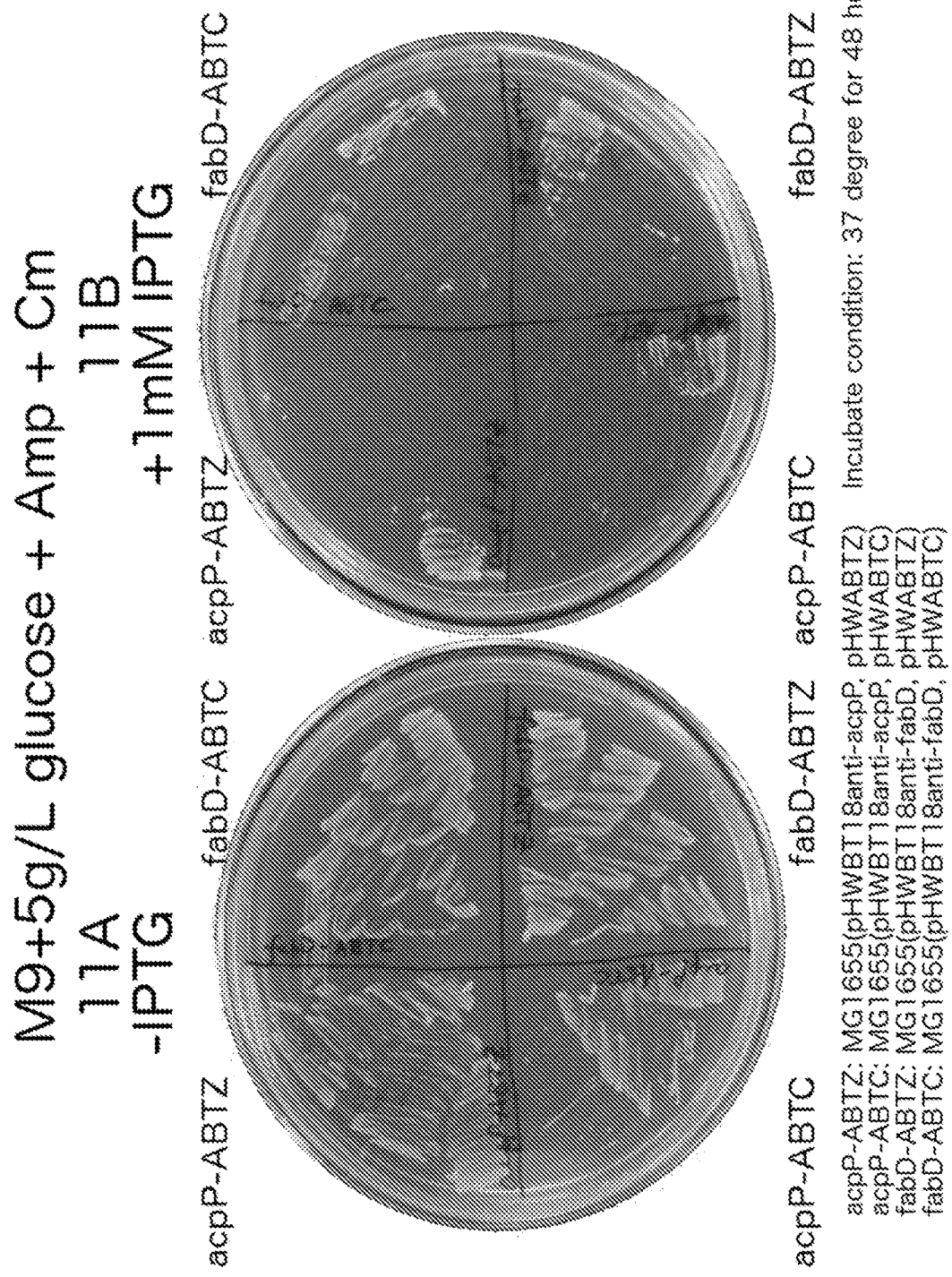
FIG. 11: Photograph showing colony formation on the IPTG free M9 plus glucose plate (11a) and on the 1 mM IPTG M9 plus glucose plate (11b).

The cells showed normal growth on normal M9-glucose plate (right bottom quadrant, FIG. 11, 11a). The cells resumed growth when butyryl-CoA was being provided, even where the expression of fabD was suppressed by the anti-sense (right bottom quadrant, FIG. 11, 11b). These results indicate that the cells were able to incorporate butyryl-CoA into the fatty acid biosynthesis pathway to form fatty acids (and hence resumed cell growth) independent of malonyl ACP.

A similar experiment was performed with the strain MG1655 (pHWBT18Anti-fabD, pHW ABTC). This strain carries an anti-sense fabD gene, and four genes that encode the enzymes for the formation of butyryl-CoA from acetyl-CoA: β-ketothiolase from *Ralstonia eutropha* H16, acetoacetyl-CoA reductase from *Ralstonia eutropha* H16, trans-enoyl-coenzyme A reductase from *Treponema denticola*, and crotonase from *Clostridium acetobutylicum*. Similar results were obtained with resumed cell growth when butyryl-CoA was being provided even where the expression of fabD was suppressed by the anti-sense (right top quadrant, FIG. 11, 11b). These results again confirm that the cells were able to incorporate butyryl-CoA into the fatty acid biosynthesis pathway to form fatty acids (and hence resumed cell growth) independent of malonyl ACP.

This third experiment demonstrates the functionality of the KASIII independent pathway with both KASIII and FabD eliminated. A single colony of strain HWK201 (pTrc99a, pHWBT18anti-fabD) or HWK201 (pHWABTZ, pHWBT18anti-fabD) was inoculated into 5 ml of LB and the experiments proceeded as described above.

The HWK201 (pHWABTZ, pHWBT18anti-fabD) strain produced more than twice fatty acids than that of the control strain HWK201 (pTrc99a, pHWBT18anti-fabD). These results further demonstrated that neither malonyl-ACP nor KASIII is essential for the KASIII independent fatty acid synthesis system, since the strain KASIII⁻ fabD⁻ strain produced higher levels of fatty acids with the four genes that encode the enzymes for the formation of butyryl-CoA from acetyl-CoA than that of the control strain that did not carry these four genes (Table 8).

TABLE 8

Concentration of fatty acid production of strains HWK201 (pTrc99a, pHWBT18anti-fabD) and HWK201 (pHWABTZ, pHWBT18anti-fabD)

| Strain | Relevant genotype | IPTG (mM) | Concentration of total fatty acid (mg/L) | | |
|---|---|---|---|---|---|
| | | | 24 h | 48 h | 72 h |
| HWK201 (pHWABTZ, pWL4T) | ΔfadD, ΔfabH, re_PhaA⁺, re_PhaB⁺, td_TER⁺, ec_FabZ⁺, rc_TE⁺ | 0.050 | 102 | 303 | 333 |
| HWK201 (pTrc99a, pHWBT18anti-fabD) | ΔfadD, ΔfabH, Anti-fabD rc_TE⁺ | 0.050 | 83 | 137 | 119 |

TABLE 8-continued

Concentration of fatty acid production of strains HWK201 (pTrc99a, pHWBT18anti-fabD) and HWK201 (pHWABTZ, pHWBT18anti-fabD)

| Strain | Relevant genotype | IPTG (mM) | Concentration of total fatty acid (mg/L) | | |
|---|---|---|---|---|---|
| | | | 24 h | 48 h | 72 h |
| HWK201 (pHWABTZ, pHWBT18anti-fabD) | ΔfadD, ΔfabH, re_PhaA⁺, re_PhaB⁺, td_TER⁺, ec_FabZ⁺, Anti-fabD rc_TE⁺ | 0.050 | 117 | 265 | 274 | re_PhaA⁺: overexpression of β-ketothiolase from *Ralstonia eutropha* H16 in pTrc99a
re_PhaB⁺: overexpression of acetoacetyl-CoA reductase from *Ralstonia eutropha* H16 in pTrc99a
td_TER⁺: overexpression of trans-enoyl-coenzyme A reductase from *Treponema denticola* in pTrc99a
ec_FabZ⁺: overexpression of 3-hydroxyacyl-ACP dehydrase from *E. coli* in pTrc99a
rc_TE⁺: overexpression of acyl-ACP thioesterase from *Ricinus communis* under the TUM3 promoter in pBAD33
ΔfadD: deactivation of acyl-CoA synthetase
ΔfabH: deactivation of β-ketoacyl-acyl carrier protein synthase III AcpP Anti-Sense This set of experiments knocks out acyl carrier protein (AcpP) functionality using antisense, thus further confirming that adding overexpressed enzymes can still allow FAS even without AcpP. This provides further options for running a KASIII independent FAS synthesis.

This first experiment demonstrated the proper functionality of the anti-sense construct, pHWBT18Anti-acpP. The strain MG1655 (pHWBT18Anti-acpP) carries the antisense-acpP gene under the control of an inducible trc promoter system and showed normal growth on normal M9-glucose plate (bottom half, FIG. 10, 10a) and no growth on IPTG supplemented M9-glucose plate (bottom half, FIG. 10, 10b). These results indicate that the anti-acpP system is functional and upon induction prevents or greatly reduces the formation of ACP-carrier protein and hence limiting cell growth.

The second experiment demonstrates that the KASIII independent pathway will function even without the ACP carrier protein when the FAS enzymes are overexpressed, likely due to the high concentration of enzymes in the cell ensuring that the synthesis continue even without ACP carrier protein transferring the growing chain to the next enzyme. Two strains, MG1655 (pHWBT18Anti-acpP, pHWABTZ) and MG1655 (pHWBT18Anti-acpP, pHWABTC), were chosen for this experiment.

The strain MG1655 (pHWBT18Anti-acpP, pHWABTZ) carries an anti-sense acpP gene, and four genes which encode the enzymes for the formation of butyryl-CoA from acetyl-CoA: β-ketothiolase from *Ralstonia eutropha* H16, acetoacetyl-CoA reductase from *Ralstonia eutropha* H16, trans-enoyl-coenzyme A reductase from *Treponema denticola*, and 3-hydroxyacyl-ACP dehydrase from *E. coli*.

The cells showed normal growth on normal M9-glucose plate (left top quadrant, FIG. 11, 11a). The cell resumed growth when butyryl-CoA was being provided even where the expression of acpP was suppressed by the anti-sense (left top quadrant, FIG. 11, 11b). These results indicate that the cells were able to incorporate butyryl-CoA into the fatty acid biosynthesis pathway to form fatty acids (and hence resumed cell growth) independent of ACP.

A similar experiment was performed with the strain MG1655 (pHWBT18Anti-acpP, pHWABTC). This strain carries an anti-sense acpP gene, and four genes that encode the enzymes for the formation of butyryl-CoA: acetyl-CoA-β-ketothiolase from *Ralstonia eutropha* H16, acetoacetyl-CoA reductase from *Ralstonia eutropha* H16, trans-enoyl-coenzyme A reductase from *Treponema denticola*, and crotonase from *Clostridium acetobutylicum*. Similar results were obtained, with resumed cell growth when butyryl-CoA was being provided, even where the expression of acpP was suppressed by the anti-sense (left bottom quadrant, FIG. 11, 11b).

These results confirm that the cells were able to incorporate butyryl-CoA into the fatty acid biosynthesis pathway to form fatty acids (and hence resumed cell growth) and furthermore that this pathway can even run independently of ACP if the enzymes are overexpressed.

This next experiment combines the KASIII mutant with the AcpP antisense. A single colony of strain HWK201 (pTrc99a, pHWBT18anti-acpP) or HWK201 (pHWABTZ, pHWBT18anti-acpP) was inoculated into 5 ml of LB and treated as above. The fatty acid concentration was quantified by a GC-FID system (Table 9).

The HWK201 (pHWABTZ, pHWBT18anti-acpP) strain produced more than twice fatty acids than that of the control strain HWK201 (pTrc99a, pHWBT18anti-acpP). These results demonstrated that ACP carrier protein is not essential for the KASIII independent fatty acid synthesis system since the strain carries the anti-sense acpP produced higher levels of fatty acids in strains with the four genes that encode the enzymes for the formation of butyryl-CoA from acetyl-CoA than the control strain that did not carry these four genes (Table 9).

In addition, the HWK201 (pHWABTZ, pHWBT18anti-acpP) strain produces a similar level of fatty acids with another control strain HWK201 (pHWABTZ, pWL4T) strain, which does not carry the anti-sense-acpP. That is, the presence of anti-sense-acpP does not affect the fatty acid production of HWK201 (pHWABTZ, pHWBT18anti-acpP) strain, which carries genes that encode enzymes that convert acetyl-CoA to butyryl-CoA to activate the KASIII independent fatty acid system.

TABLE 9

Concentration of fatty acid production of strains HWK201 (pTrc99a, pHWBT18anti-acpP) and HWK201 (pHWABTZ, pHWBT18anti-acpP)

| Strain | Relevant genotype | IPTG (mM) | Concentration of total fatty acid (mg/L) | | |
|---|---|---|---|---|---|
| | | | 24 h | 48 h | 72 h |
| HWK201 (pHWABTZ, pWL4T) | ΔfadD, ΔfabH, re_PhaA+, re_PhaB+, td_TER+, ec_FabZ+, rc_TE+ | 0.050 | 102 | 303 | 333 |
| HWK201 (pTrc99a, pHWBT18anti-acpP) | ΔfadD, ΔfabH, Anti- acpP rc_TE+ | 0.050 | 108 | 156 | 151 |
| HWK201 (pHWABTZ, pHWBT18anti-acpP) | ΔfadD, ΔfabH, re_PhaA+, re_PhaB+, td_TER+, ec_FabZ+, Anti- acpP rc_TE+ | 0.050 | 21 | 293 | 392 | re_PhaA+: overexpression of β-ketothiolase from *Ralstonia eutropha* H16 in pTrc99a
re_PhaB+: overexpression of acetoacetyl-CoA reductase from *Ralstonia eutropha* H16 in pTrc99a
td_TER+: overexpression of trans-enoyl-coenzyme A reductase from *Treponema denticola* in pTrc99a
ec_FabZ+: overexpression of 3-hydroxyacyl-ACP dehydrase from *E. coli* in pTrc99a
rc_TE+: overexpression of acyl-ACP thioesterase from *Ricinus communis* under the TUM3 promoter in pBAD33
ΔfadD: deactivation of acyl-CoA synthetase
ΔfabH: deactivation of β-ketoacyl-acyl carrier protein synthase III AccA Antisense This first experiment demonstrated the proper functionality of the anti-sense construct for AccA—acetyl-CoA carboxylase—which catalyzes the irreversible carboxylation of acetyl-CoA to produce malonyl-CoA, thus providing further proof that the fatty acids produced herein truly are via a KASIII independent pathway.

Figure 8:
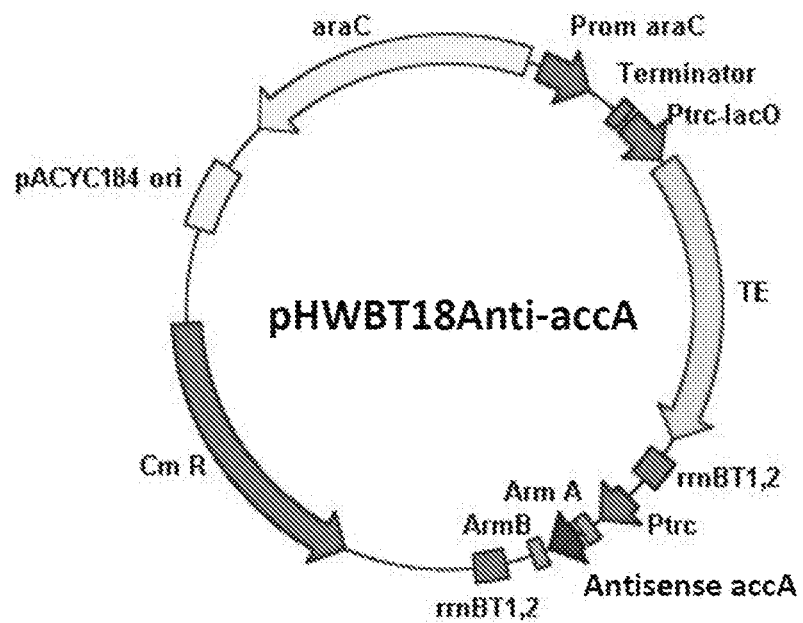
FIG. 8: Schematic diagram of pHWBT18Anti-accA, which is modified from pHWBT18Anti-fabD. Abbreviations: TE gene from *R. communis*; Antisense accA gene, antisense sequence of accA gene from *E. coli*; ArmA and ArmB, forming paired-termini to antisense RNA after expression; pTrc-lacO, trc promoter without lacO binding site; pTrc, trc promoter; lad, lac operon repressor; Amp, ampicillin resistant gene; pACYC184 ori, origin of replication of plasmid pACYC184, rrnBT1,2, transcriptional terminator of rrnB.
Figure 12:
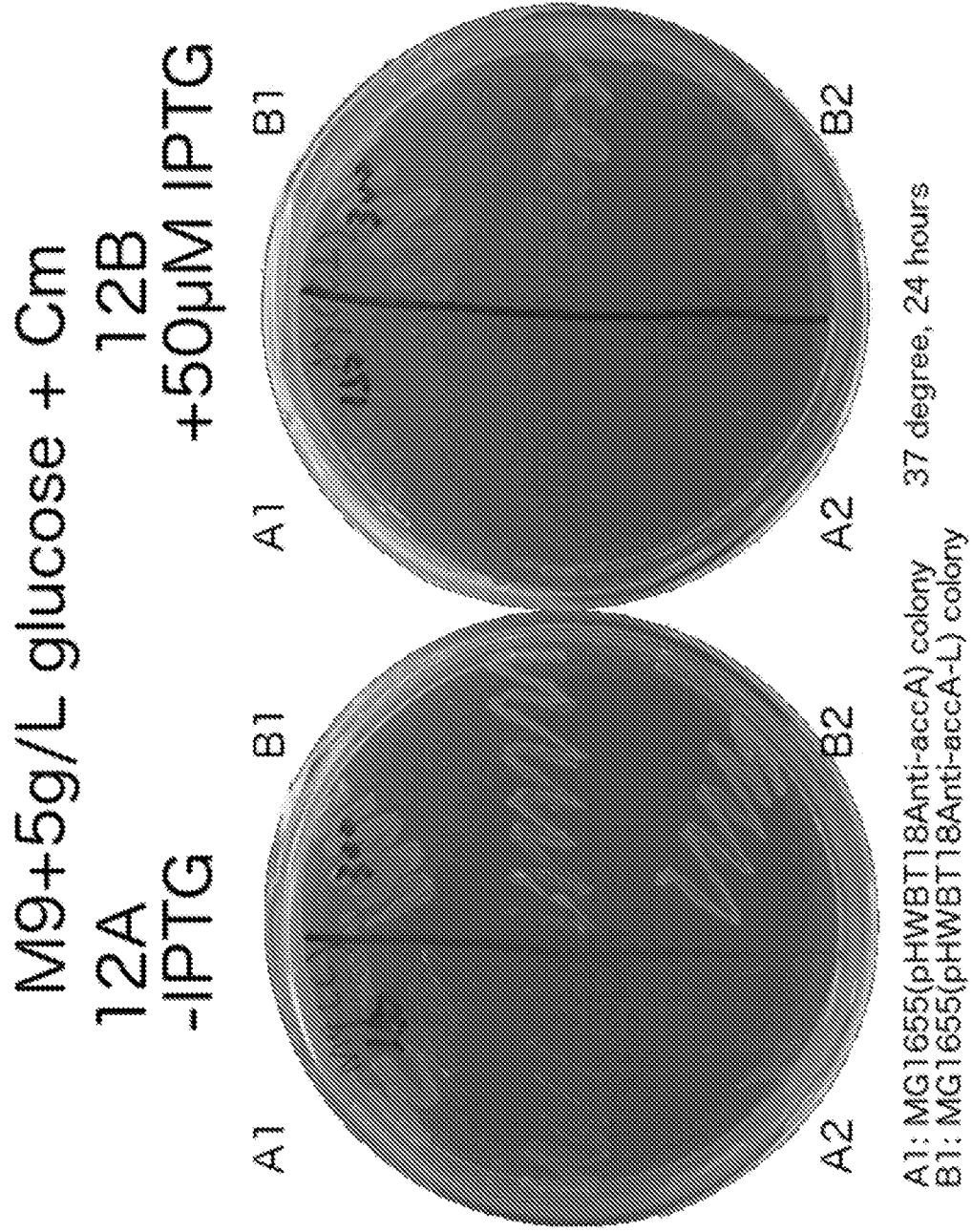
FIG. 12: Photograph showing colony formation on the IPTG free M9 plus glucose plate (12a) and on the 50 uM IPTG M9 plus glucose plate (12b) at 24 h. The strain MG1655 (pHWBT18Anti-accA) bearing a 150 bp antisense DNA fragment performs much better than that of MG1655 (pHWBT18Anti-accA-L), which carries a 300 bp antisense DNA fragment in inhibiting cell growth. The cell growth was limited for the strain MG1655 (pHWBT18Anti-accA) even without any IPTG due to leakage transcription (12a-A1) and was very much limited in the presence of 50 micro-M IPTG (12b-A1). The growth of the strain MG1655 (pHWBT18Anti-accA-L) was much better with any IPTG addition (12a-B1) but was also inhibited in the presence of IPTG (12b-B1).

The construct is pHWBT18Anti-accA (FIG. 8), which can inhibit cell growth in the presence of the inducer IPTG. The strain MG1655 (pHWBT18Anti-accA) bearing a 150 bp antisense DNA fragment performs much better than that of MG1655 (pHWBT18Anti-accA-L), which carries a 300 bp antisense DNA fragment in inhibiting cell growth. Cell growth was limited for the strain MG1655 (pHWBT18Anti-accA) even without any IPTG due to leaky transcription (FIG. 12, 12a-A1), but was very much limited in the presence of 50 micro-M IPTG (FIG. 12, 12b-A1). The growth of the strain MG1655 (pHWBT18Anti-accA-L) was much better with any IPTG addition (FIG. 12, 12a-B1), but was also inhibited in the presence of IPTG (FIG. 12, 12b-B1).

These results indicate that the anti-accA antisense is functional and upon induction prevents or greatly reduces the formation of malonyl-CoA, hence limiting cell growth. The next experiment shows that the KASIII independent FAS can rescue the poor cell growth caused by lack of AccA.

A single colony of following eight strains: HWK201 (pTrc99a, pHWBT18anti-accA), HWK201 (pHWABTZ, pHWBT18anti-accA), HWK201 (pHWL4T), HWK201 (pHWBT18anti-accA), MG1655 (pHWBT18), MG1655 (pHWBT18anti-accA), MG1655 (pTrc99a, pHWBT18anti-accA), and MG1655 (pHWABTZ, pHWBT18anti-accA), were inoculated into 5 ml of LB and the experiment proceeded as above. The fatty acid concentration was quantified by a GC-FID system (Table 10).

For the HWK201 host strain, the presence of antisense-accA greatly reduces the production of fatty acids, from 61 to 10 mg/L. Inducing the plasmid pHWABTZ carrying the genes re phaA, re phaB, td ter, ec fabZ that encodes four enzymes to convert acetyl-CoA to butyryl-CoA, the fatty acid production by the strain HWK201 (pHWABTZ, pHWBT18anti-accA) is significantly increased to more 150 mg/L, even in the presence of the anti-sense accA (Table 10). Similar results were obtained with the MG1655 host strains. The strain MG1655 (pHWABTZ, pHWBT18anti-accA) produced 643 mg/L of fatty acid, which is very similar to that of the MG1655 (pHWBT18), which does not carry the anti-sense accA.

The results show that the presence of antisense-accA (resulting in reduced malonyl-CoA availability) does not shut down the fatty acid production by the strain HWK201 (pHWABTZ, pHWBT18anti-accA), which carries genes that encode enzymes to convert acetyl-CoA to butyryl-CoA and activates the KASIII independent fatty acid system. The results also suggest HWK201 (pHWABTZ, pHWBT18) can use both acetyl-CoA and malonyl-CoA for the chain length elongation of fatty acids.

TABLE 10

Concentration of fatty acid production of strains HWK201 (pTrc99a, pHWBT18anti-accA), HWK201 (pHWABTZ, pHWBT18anti-accA), HWK201 (pHWL4T), HWK201 (pHWBT18anti-accA), MG1655(pHWBT18), MG1655 (pHWBT18anti-accA), MG1655 (pTrc99a, pHWBT18anti-accA), MG1655 (pHWABTZ, pHWBT18anti-accA)

| Strain | Relevant genotype | IPTG (mM) | Concentration of total fatty acid (mg/L) 24 h | 48 h | 72 h |
|---|---|---|---|---|---|
| HWK201 (pHWL4T) | ΔfadD, ΔfabH, rc_TE+ | 0.050 | — | 52 | 61 |
| HWK201 (pHWBT18anti-accA) | ΔfadD, ΔfabH, Anti-accA rc_TE+ | 0.050 | <10 | <10 | <10 |
| HWK201 (pTrc99a, pHWBT18anti-accA) | ΔfadD, ΔfabH, Anti-accA rc_TE+ | 0.050 | 115 | 138 | 134 |
| HWK201 (pHWABTZ, pHWBT18anti-accA) | ΔfadD, ΔfabH, re_PhaA+, re_PhaB+, td_TER+, ec_FabZ+, Anti-accA rc_TE+ | 0.050 | 154 | 191 | 192 |
| MG1655 (pHWBT18) | rc_TE+ | 0.050 | 778 | 960 | 976 |
| MG1655 (pHWBT18anti-accA) | Anti-accA rc_TE+ | 0.050 | 325 | 392 | 380 |
| MG1655 (pTrc99a, pHWBT18anti-accA) | Anti-accA rc_TE+ | 0.050 | 162 | — | — |
| MG1655 (pHWABTZ, pHWBT18anti-accA) | re_PhaA+, re_PhaB+, td_TER+, ec_FabZ+, Anti-accA rc_TE+ | 0.050 | 643 | — | — | re_PhaA+: overexpression of β-ketothiolase from *Ralstonia eutropha* H16 in pTrc99a
re_PhaB+: overexpression of acetoacetyl-CoA reductase from *Ralstonia eutropha* H16 in pTrc99a
td_TER+: overexpression of trans-enoyl-coenzyme A reductase from *Treponema denticola* in pTrc99a
ec_FabZ+: overexpression of 3-hydroxyacyl-ACP dehydrase from *E. coli* in pTrc99a
rc_TE+: overexpression of acyl-ACP thioesterase from *Ricinus communis* under the TUM3 promoter in pBAD33
ΔfadD: deactivation of acyl-CoA synthetase
ΔfabH: deactivation of β-ketoacyl-acyl carrier protein synthase III

Fats not Made by Reversal Beta-Oxidation Cycle

We have shown above that fats made in our cells truly are KASIII independent using a KASIII mutant, as well as using antisense for AccP, AccA, and FabD in various combinations. However, since the pivotal work of Ramon Gonzalez at William Marsh Rice University, it remained formally possible that the fats were being produced by a reverse beta-oxidation cycle. This experiment was designed to eliminate that possibility.

The enzyme acyl-CoA dehydrogenase catalyzes a key reaction in the fatty acid beta-oxidation cycle. A fadE mutant was created to demonstrate the fatty acid production described in this invention is not by the reversal of beta-oxidation (R-BOX) cycle, but did in fact proceed by the KASIII independent pathway. A triple mutant strain, XZK108, was constructed which is a fadE, fadD (acyl-CoA synthetase) and fabH (beta-Ketoacyl-ACP synthase III aka KASIII) triple mutant.

The data in Table 11 proves that the fats are not being made using R-BOX, but made using the new KASIII-independent pathway. The XZK108 (pHWABTZ, pWL4T) strain with deactivation of acyl-CoA dehydrogenase enzyme (ΔfadE) produced similar quantity of fatty acid as its parent strain (pHWABTZ, pWL4T). Since acyl-CoA dehydrogenase (fadE) is a key enzyme involved in the fatty acid beta-oxidation pathway, the results prove that the fat is made through the intended KASIII independent pathway.

TABLE 11

Concentration of fatty acid production of strains HWK201 (pHWABTZ, pWL4T), XZK108 (pTrc99a, pWL4T) and XZK108 (pHWABTZ, pWL4T)

| Strain | Relevant genotype | IPTG (mM) | Concentration of total fatty acid (mg/L) 24 h | 48 h | 72 h |
|---|---|---|---|---|---|
| HWK201 (pHWABTZ, pWL4T) | ΔfadD, ΔfabH, re_PhaA+, re_PhaB+, td_TER+, ec_FabZ+, rc_TE+ | 0.050 | 102 | 303 | 333 |
| XZK108 (pTrc99a, pWL4T) | ΔfadD, ΔfabH, ΔfadE rc_TE+ | 0.050 | 65 | 58 | 56 |
| XZK108 (pHWABTZ, pWL4T) | ΔfadD, ΔfabH, ΔfadE, re_PhaA+, re_PhaB+, td_TER+, ec_FabZ+, rc_TE+ | 0.050 | 249 | 313 | 320 | re_PhaA+: overexpression of β-ketothiolase from *Ralstonia eutropha* H16 in pTrc99a
re_PhaB+: overexpression of acetoacetyl-CoA reductase from *Ralstonia eutropha* H16 in pTrc99a
td_TER+: overexpression of trans-enoyl-coenzyme A reductase from *Treponema denticola* in pTrc99a
ec_FabZ+: overexpression of 3-hydroxyacyl-ACP dehydrase from *E. coli* in pTrc99a
rc_TE+: overexpression of acyl-ACP thioesterase from *Ricinus communis* under the TUM3 promoter in pBAD33
ΔfadD: deactivation of acyl-CoA synthetase
ΔfabH: deactivation of β-ketoacyl-acyl carrier protein synthase III
ΔfadE: deactivation of acyl-CoA dehydrogenase enzyme

Hydroxy Fatty Acid Production

Figure 13:
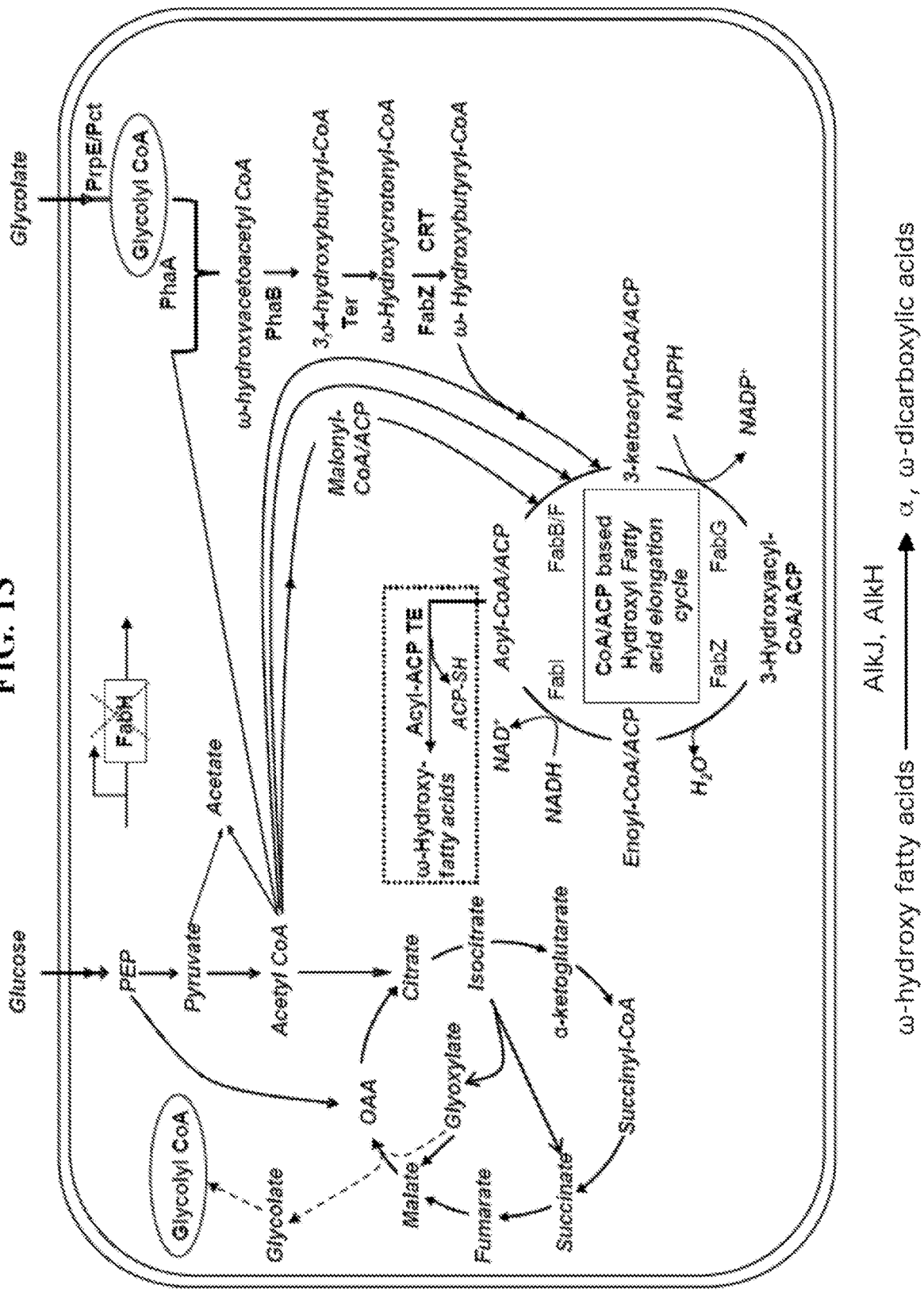
FIG. 13: An example of KASIII independent hydroxy fatty acid and dicarboxylic acids synthesis pathway.
Figure 14:
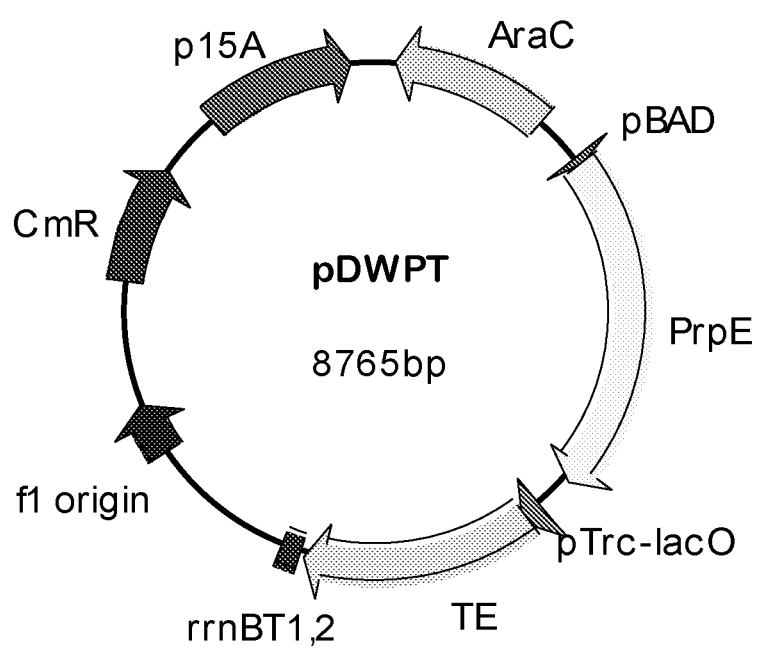
FIG. 14: Schematic diagram of the plasmid pDWPT. Abbreviations: prpE gene from *Salmonella enterica*; TE gene from *R. communis*; pBAD, Ara promoter; pTrc-lacO, trc promoter without lacO binding site; f1 origin, origin from a f1 phage; CmR, chloramphenicol resistant gene; p15A origin, origin of replication of plasmid p15A, rrnBT1,2, transcriptional terminator of rrnB.
Figure 15:
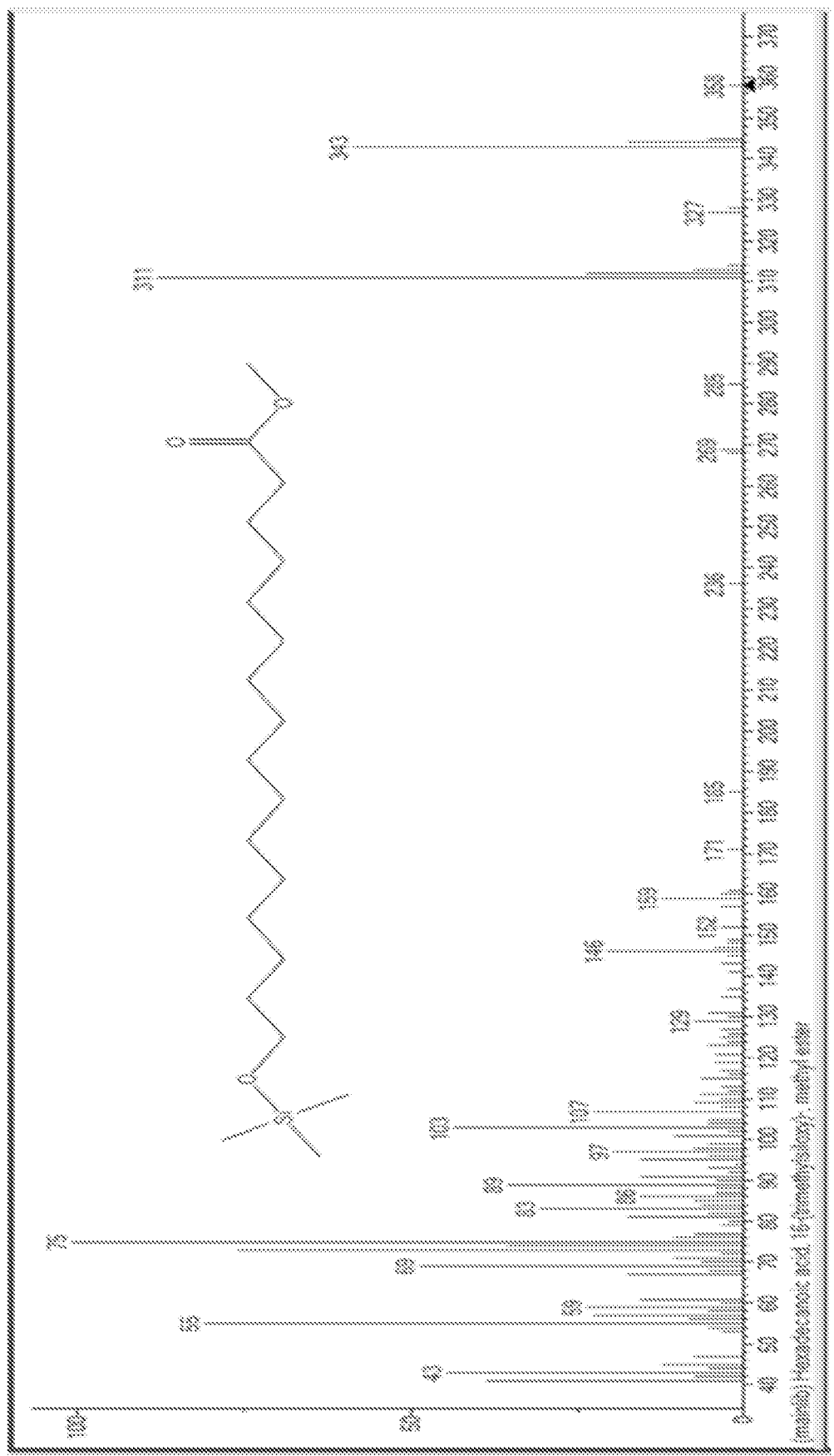
FIG. 15: Fragmentation patterns of derivatized 16-Hydroxyhexadecanoic acid (hexadecanoic acid, 16-(trimethylsiloxy)-, methyl ester); the spectrum is from NIST/EPA/NIH Spectral Library).
Figure 16:
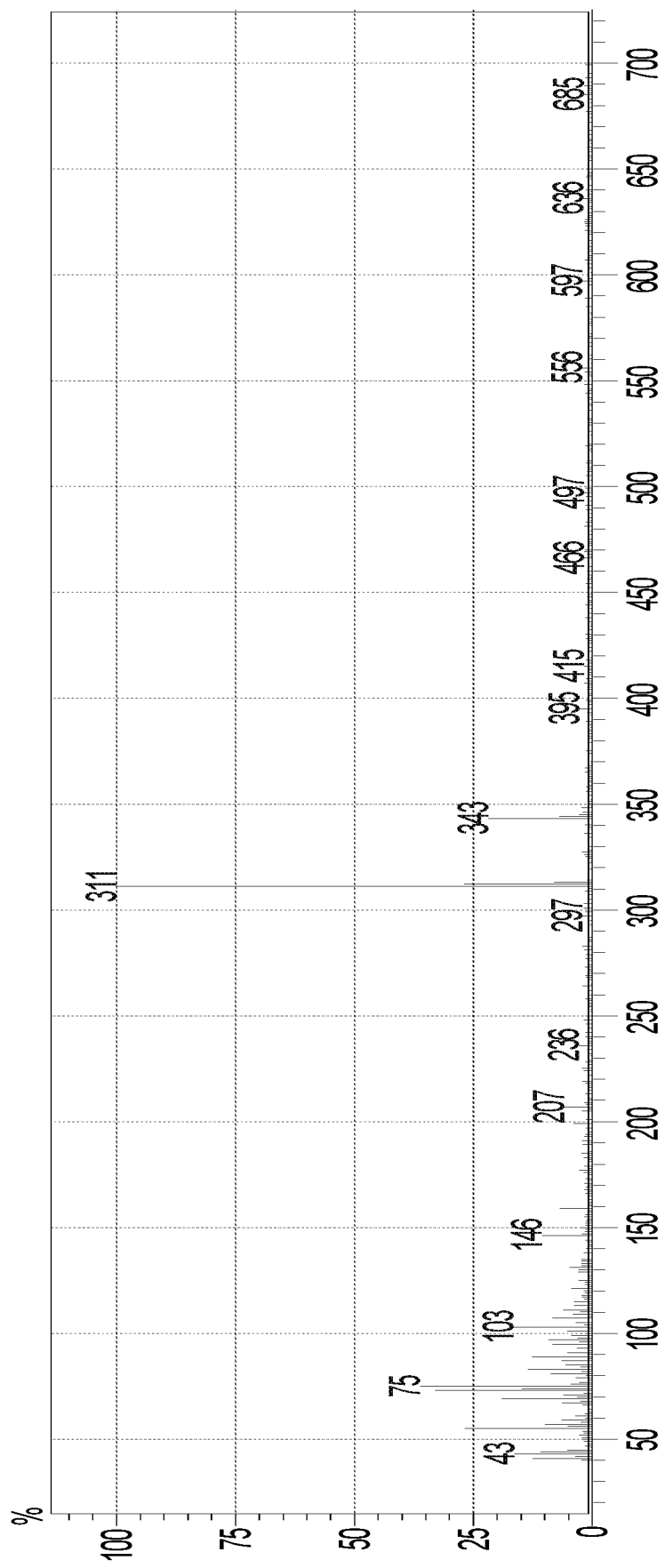
FIG. 16: Fragmentation patterns of derivatized 16-Hydroxyhexadecanoic acid of sample (hexadecanoic acid, 16-(trimethylsiloxy)-, methyl ester also known as methyl 16-hydroxy-hexadecanoate-trimethylsilyl ether).
Figure 17:
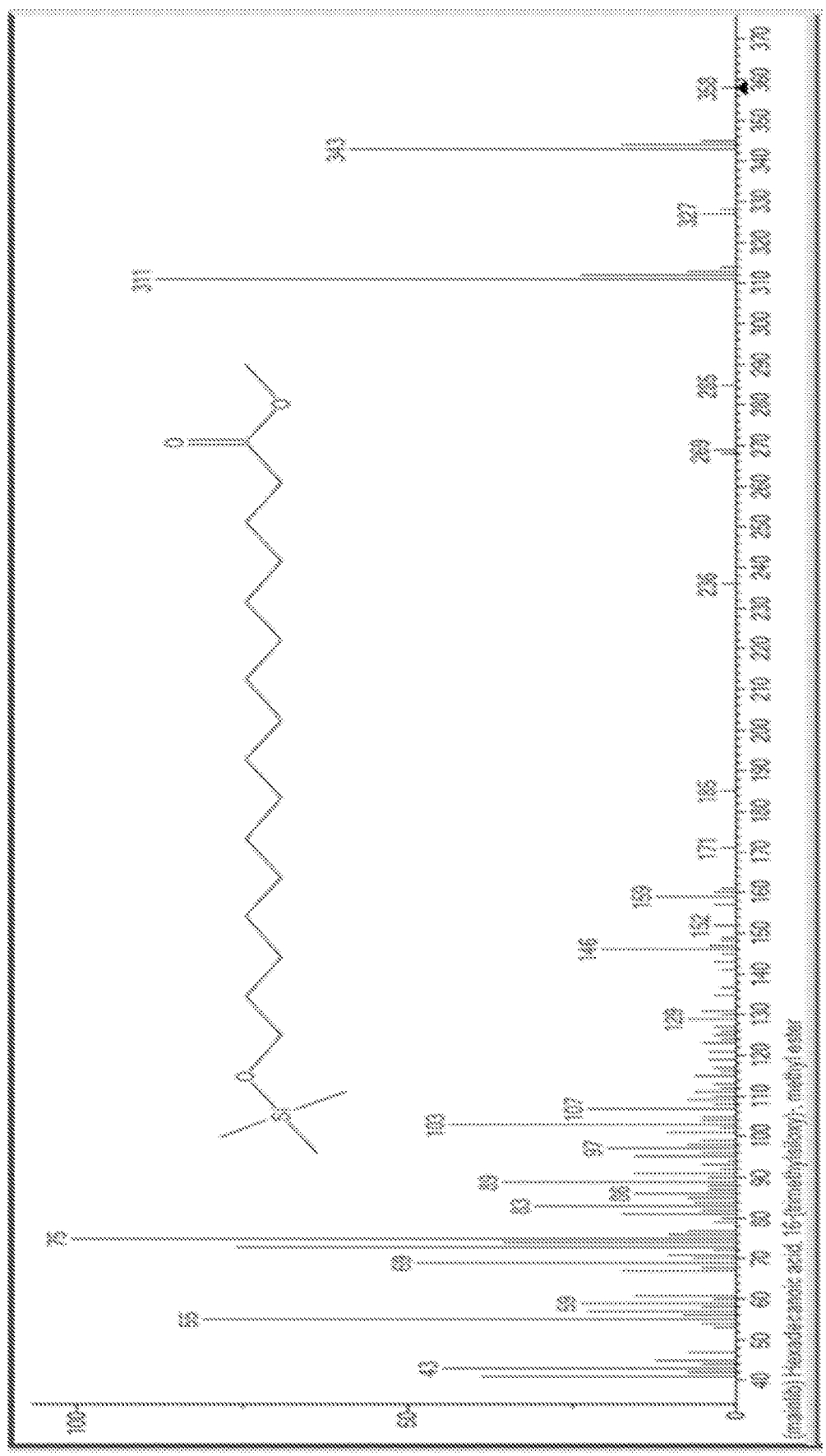
FIG. 17: Fragmentation patterns of derivatized 16-Hydroxyhexadecanoic acid (hexadecanoic acid, 16-(trimethylsiloxy)-, methyl ester); the spectrum is from NIST/EPA/NIH Spectral Library).
Figure 18:
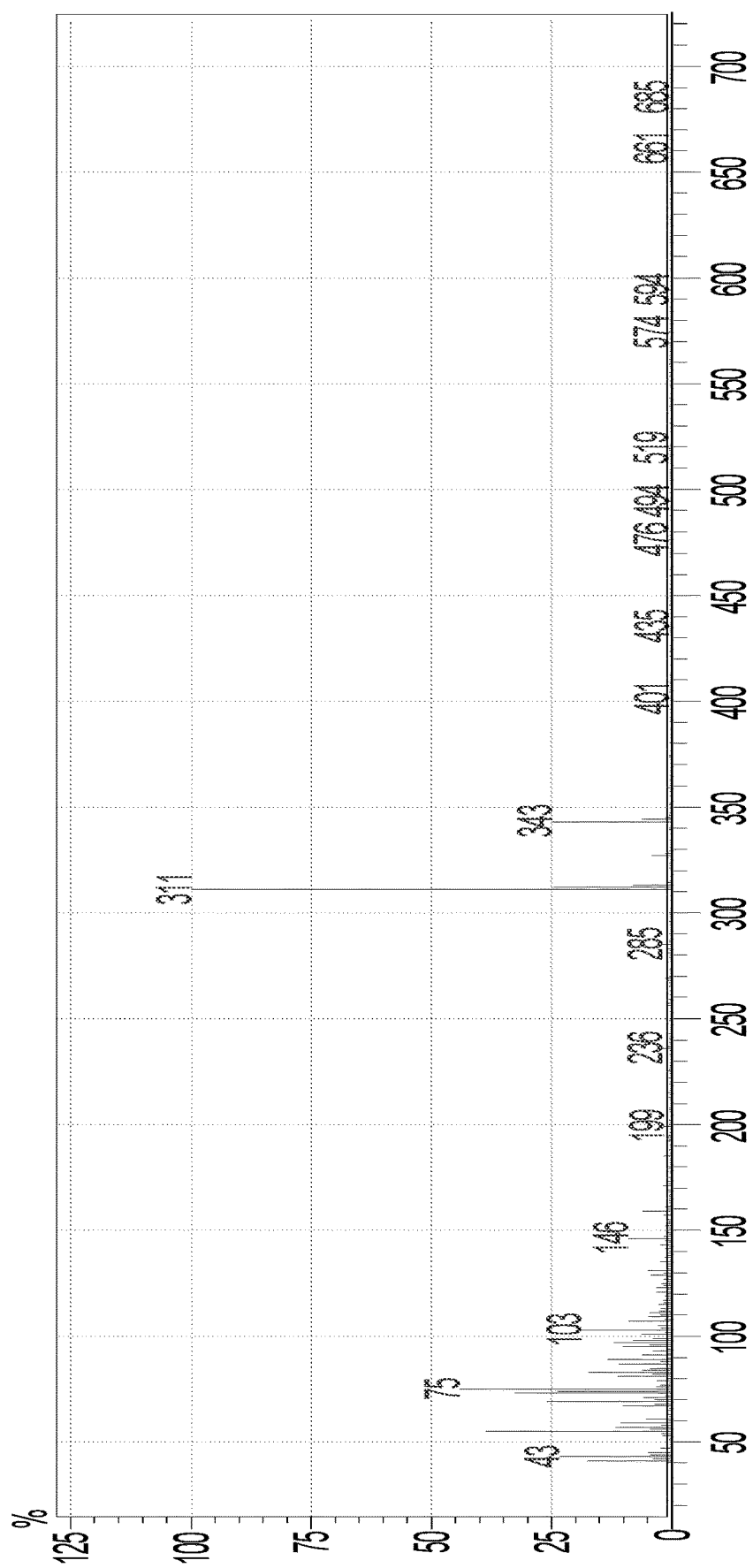
FIG. 18: Fragmentation patterns of 16-Hydroxyhexadecanoic acid of sample.
Figure 19:
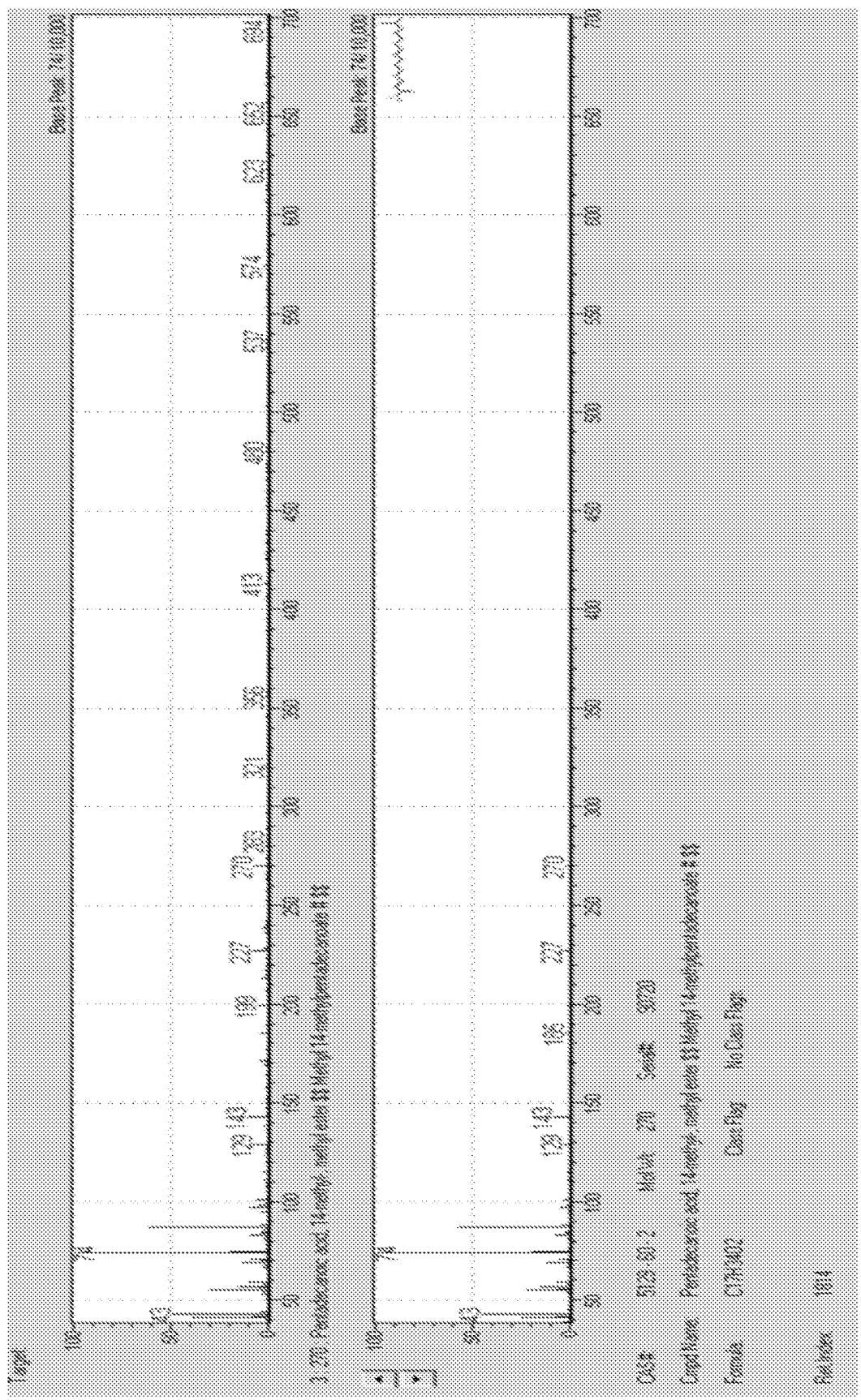
FIG. 19: Fragmentation patterns of derivatized 14-methyl-pentadecanoic acid from fermentation sample (Pentadecanoic acid, 14-methyl-, methyl ester). Top panel: spectrum from fermentation sample; bottom panel: spectrum from NIST/EPA/NIH Spectral Library.

The biosynthesis of hydroxy fatty acid was used to demonstrate the ability to synthesize bi-functional molecules using the invention. The priming molecule (glycolyl CoA) is supplied by the activation of externally added glycolic acid using propionyl-CoA synthase (prpE) from *Salmonella enterica*, which activates the glycolic acid with coA. The hydroxy acetyl-CoA is then converted to hydroxy butyryl-CoA before entering into the KASIII independent fatty acid synthesis system (FIG. 13). Plasmid pDWPT, which carries the acyl-ACP thioesterase (TE) from *Ricinus communis* and propionyl-CoA synthase (prpE) from *Salmonella enterica*, was constructed (FIG. 14).

The control strains carrying the plasmid only with the TE (pWL1T) or the plasmid with TE and the propionyl-CoA synthase (pDWPT) does not produce detectable quantities of omega-hydroxyhexadecanoic acid (or 16-hydroxyhexadecanoic acid) with or without addition of glycolic acid to the media. This indicates that the particular primer needs help entering the KASIII-independent pathway.

For the strain HWK201 (pHWABTC, pDWPT), which carries a plasmid with acyl-ACP thioesterase and the propionyl-CoA synthase (pDWPT) as well as another plasmid with β-ketothiolase, acetoacetyl-CoA reductase, trans-enoyl-coenzyme A reductase, and 3-hydroxyacyl-ACP dehydrase (pHWABTC) produces significant quantity of omega-hydroxyhexadecanoic acid when the glycolic acid starter molecule was added to the media (Table 12). The same HWK201 (pHWABTC, pDWPT) strain does not produce detectable quantities of 16-hydroxyhexadecanoic acid when no glycolic acid was added (Table 12). The fragmentation spectra of derivatized 16-Hydroxyhexadecanoic acid of the sample show similar patterns to that from the NIST/EPA/NIH Spectral Library, proving the identity of the molecule (see FIG. 15-19 for various spectra).

These results demonstrated that omega hydroxy fatty acid can be produced by KASIII deficient strain using the native fatty acid cycle if the primer pathway to convert the glycolic acid starter molecule to an appropriate primer is added. Furthermore, these results demonstrated that: (1) propionyl-CoA synthase (prpE) from *Salmonella enterica* can catalyze the reaction from glycolic acid to glycolyl-CoA; (2) β-ketothiolase, acetoacetyl-CoA reductase, trans-enoyl-coenzyme A reductase, and 3-hydroxyacyl-ACP dehydrase can elongate glycolyl-CoA to hydroxy butyryl-CoA; and (3) the native fatty synthesis can use the resulting hydroxy butyryl-CoA as the initiating primer molecule leading to the production of 16-hydroxyhexadecanoic acid with 6 turns of the native FAS cycle.

TABLE 12

Concentration of hydroxy fatty acid production of strain HWK201 (pHWABTC, pDWPT), HWK201 (pXZ18), and HWK201 (pTrc99a, pDWPT) with and without glycolic acid addition

| Strain | Relevant genotype | IPTG (mM)/ arabinose (mM) | glycolic acid (g/L) | Concentration of omega-hydroxy-hexadecanoic acid (mg/L) 72 h |
|---|---|---|---|---|
| HWK201 (pHWABTC, pDWPT) | ΔfadD, ΔfabH, re_PhaA+, re_PhaB+, td_TER+, ca_CRT+, se_PrpE+, rc_TE+ | 0.05/10 | 0 | Below detection limit |
| HWK201 (pHWABTC, pDWPT) | ΔfadD, ΔfabH, re_PhaA+, re_PhaB+, td_TER+, ca_CRT+, se_PrpE+, rc_TE+ | 0.05/10 | 5 | 169.3 |
| HWK201 (pXZ18) | ΔfadD, ΔfabH, rc_TE+ | 0.05/0 | 0 | Below detection limit |
| HWK201 (pWL1T) | ΔfadD, ΔfabH, rc_TE+ | 0/0 | 5 | Below detection limit |
| HWK201 (pTrc99a, pDWPT) | ΔfadD, ΔfabH, Se PrpE rc_TE+ | 0.05/10 | 0 | Below detection limit |
| HWK201 (pTrc99a, pDWPT) | ΔfadD, ΔfabH, Se PrpE rc_TE+ | 0.05/10 | 5 | Below detection limit | re_PhaA+: overexpression of β-ketothiolase from *Ralstonia eutropha* H16 in pTrc99a
re_PhaB+: overexpression of acetoacetyl-CoA reductase from *Ralstonia eutropha* H16 in pTrc99a
td_TER+: overexpression of trans-enoyl-coenzyme A reductase from *Treponema denticola* in pTrc99a
ca_CRT+: overexpression of crotonase from *Clostridium acetobutylicum* in pTrc99a
rc_TE+: overexpression of acyl-ACP thioesterase from *Ricinus communis* under the TUM3 promoter in pBAD33
se_PrpE+: overexpression of propionyl-CoA synthase (prpE) from *Salmonella enterica*
ΔfadD: deactivation of acyl-CoA synthetase
ΔfabH: deactivation of β-ketoacyl-acyl carrier protein synthase III This second experiment demonstrates using a different primer pathway to illustrate the wide applicability of the KASIII independent FAS pathway. The starter molecule (glycolyl CoA) was supplied by the activation of externally added glycolic acid using propionyl-CoA synthase (prpE) from *Salmonella enterica*. However, the crotonase from *Clostridium acetobutylicum* (Ca CRT) substituted by the 3-hydroxyacyl-ACP dehydrase from *E. coli* (ec FabZ) herein. Plasmid pDWPT (FIG. 14), which carries the acyl-ACP thioesterase from *Ricinus communis* and propionyl-CoA synthase (prpE) from *Salmonella enterica*, was also used.

A single colony of strain HWK201 (pHWABTZ, pDWPT) or HWK201 (pWL1T) was inoculated into 5 ml of LB and the experiment proceeded as above. Similar to the prior experiment, the control strains carrying the plasmid only with the acyl-ACP thioesterase (pWL1T) or the plasmid with acyl-ACP thioesterase and the propionyl-CoA synthase (pDWPT) does not produce detectable quantities of omega-hydroxyhexadecanoic acid (or 16-hydroxyhexadecanoic acid) with or without addition of glycolic acid.

However, re-placing crotonase from *C. acetobutylicum* (Ca CRT) with the 3-hydroxyacyl-ACP dehydrase from *E. coli* (ec FabZ) yielded higher concentration of omega-hydroxyhexadecanoic acid when glycolic acid was added (Table 13a), possibly because the enzyme was more active with this particular substrate, producing more primer. The same HWK201 (pHWABTZ, pDWPT) strain does not produce detectable quantities of 16-hydroxyhexadecanoic acid when no glycolic acid was added (Table 13a).

Similar to the previous experiment, these results demonstrated that production of omega fatty acid by KASIII deficient strain using the native fatty acid cycle. In addition, these results further demonstrated that: (1) propionyl-CoA synthase (prpE) from *Salmonella enterica* can catalyze the reaction from glycolic acid to glycolyl-CoA; (2) β-ketothiolase, acetoacetyl-CoA reductase, trans-enoyl-coenzyme A reductase, and 3-hydroxyacyl-ACP dehydrase can elongate glycolyl-CoA to hydroxy butyryl-CoA; and (3) the native fatty synthesis can use the hydroxy butyryl-CoA as the starting molecule leading to the production of 16-hydroxy-hexadecanoic acid.

One of the advantages of the KASIII independent FAS cycle is demonstrated in Table 13b where the background of even chain length fatty acids is produced at very low levels. This is because the KASIII mutant strain can make normal fatty acid using acetyl-CoA as the primer molecule only at a very low level. Hence, the fatty acid elongation cycle is mainly used by the KASIII independent system to make functionalized fatty acids. This means that functionalized fatty acids made with the KASIII independent system will be more pure in the KASIII mutant background.

TABLE 13a

Concentration of hydroxy fatty acid production of strains HWK201 (pHWABTZ, pDWPT), HWK201 (pWL1T), (pTrc99a, pDWPT) with and without glycolic acid

| Strain | Relevant genotype | IPTG (mM)/ arabinose (mM) | glycolic acid (g/L) | Concentration of omega-hydroxy-hexadecanoic (mg/L) 72 h |
|---|---|---|---|---|
| HWK201 (pHWABTZ, pDWPT) | ΔfadD, ΔfabH, re_PhaA+, re_PhaB+, td_TER+, ec_FabZ+, se_PrpE+, rc_TE+ | 0.05/10 | 0 | ND |
| HWK201 (pHWABTZ, pDWPT) | ΔfadD, ΔfabH, re_PhaA+, re_PhaB+, td_TER+, ec_FabZ+, se_PrpE+, rc_TE+ | 0.05/10 | 5 | 407.9 |
| HWK201 (pWL1T) | ΔfadD, ΔfabH, rc_TE+ | 0/0 | 0 | ND |
| HWK201 (pWL1T) | ΔfadD, ΔfabH, rc_TE+ | 0/0 | 5 | ND |
| HWK201 (pTrc99a, pDWPT)* | ΔfadD, ΔfabH, se_PrpE+, rc_TE+ | 0.05/10 | 0 | ND |
| HWK201 (pTrc99a, pDWPT)* | ΔfadD, ΔfabH, se_PrpE+, rc_TE+ | 0.05/10 | 5 | ND | re_PhaA+: overexpression of β-ketothiolase from *Ralstonia eutropha* H16 in pTrc99a
re_PhaB+: overexpression of acetoacetyl-CoA reductase from *Ralstonia eutropha* H16 in pTrc99a
td_TER+: overexpression of trans-enoyl-coenzyme A reductase from *Treponema denticola* in pTrc99a
ec_FabZ+: overexpression of 3-hydroxyacyl-ACP dehydrase from *E. coli* in pTrc99a
rc_TE+: overexpression of acyl-ACP thioesterase from *Ricinus communis* under the TUM3 promoter in pBAD33
se_PrpE+: overexpression of propionyl-CoA synthase (prpE) from *Salmonella enterica*
ΔfadD: deactivation of acyl-CoA synthetase
ΔfabH: deactivation of β-ketoacyl-acyl carrier protein synthase III
*data from Table 12; ND—not detected - below detection limit TABLE 13b Concentration of fatty acid production of strains HWK201 (pHWABTZ, pDWPT) and HWK201 (pWL1T) and HWK201 (pTrc99a, pDWPT)

| Strain | Relevant genotype | IPTG (mM)/ arabinose (mM) | glycolic acid (g/L) | Concentration of fatty acid (mg/L) at 72 h | | |
|---|---|---|---|---|---|---|
| | | | | C14 | C16 | C16:1 |
| HWK201 (pWL1T)* | ΔfadD, ΔfabH, rc_TE+ | 0/0 | 5 | ND | 21.9 | 8.1 |
| HWK201 (pTrc99a, pDWPT)* | ΔfadD, ΔfabH, se_PrpE+ rc_TE+ | 0.05/10 | 5 | ND | 20.2 | 15.1 |
| HWK201 (pHWABTZ, pDWPT) | ΔfadD, ΔfabH, re_PhaA+, re_PhaB+, td_TER+, ec_FabZ+, se_PrpE+ rc_TE+ | 0.05/10 | 5 | ND | 127.1 | 86.7 | re_PhaA+: overexpression of β-ketothiolase from *Ralstonia eutropha* H16 in pTrc99a
re_PhaB+: overexpression of acetoacetyl-CoA reductase from *Ralstonia eutropha* H16 in pTrc99a
td_TER+: overexpression of trans-enoyl-coenzyme A reductase from *Treponema denticola* in pTrc99a
ec_FabZ+: overexpression of 3-hydroxyacyl-ACP dehydrase from *E. coli* in pTrc99a
rc_TE+: overexpression of acyl-ACP thioesterase from *Ricinus communis* under the TUM3 promoter in pBAD33
se_PrpE+: overexpression of propionyl-CoA synthase (prpE) from *Salmonella enterica*
ΔfadD: deactivation of acyl-CoA synthetase
ΔfabH: deactivation of β-ketoacyl-acyl carrier protein synthase III
ND—not detected - below detection limit Branched Fatty Acid Production The versatility of the KASIII independent synthesis pathway was demonstrated by using a different substrate in order to produce branched chain fatty acids. In this study, the biosynthesis of omega methyl fatty acids was used to demonstrate the ability of synthesizing branched fatty acid cycle by supplying the substrate isobutyrate.

The priming molecule (isobutyryl CoA) in the following example was supplied by the activation of externally added isobutyrate using propionyl-CoA synthase (prpE) from *Salmonella enterica*. The isobutyryl CoA is then extended to longer chain branched fatty acids by the FAS cycle (similar to that shown in FIG. 13). The plasmid pDWPT, which carries the acyl-ACP thioesterase from *Ricinus communis* and propionyl-CoA synthase (prpE) from *Salmonella enterica*, is used (FIG. 14). Notice that here, fewer genes were needed to activate the primer for the KASIII independent FAS.

A single colony of strain HWK201 (pDWPT) was inoculated into 5 mL of LB and the experiment proceeded as above, except the effect of addition of 2.64 g/L (30 mM) of isobutyrate was investigated. The fatty acid concentrations were quantified by a GC/FID and a GC/MS system, respectively.

CoA) in the following example was supplied by the activation of externally added starter molecule propionic acid, which was activated to the primer form using propionyl-CoA synthase (prpE) from *Salmonella enterica*. The propionyl CoA primer was then extended to longer chain fatty acids by FAS (similar to that shown in FIG. 13).

The plasmid pHWABTZ carrying the genes re phaA, re phaB, td ter, ec fabZ which encode for enzymes to convert acetyl-CoA to butyryl-CoA and the plasmid pDWPT, which carries the acyl-ACP thioesterase from *Ricinus communis* and propionyl-CoA synthase (prpE) from *Salmonella enterica*, was used (similar to FIG. 14). In addition, plasmid pHWABTC was also used in place of pHWABTZ.

A single colony of strain HWK201 (pHWABTZ, pDWPT), HWK201 (pHWABTC pDWPT), HWK201 (pW1T), or HWK201 (pDWPT) was inoculated into 5 ml of LB and the experiment proceeded as above, except the effect of addition of 0.89 g/L (12 mM) of propionic acid was investigated as a starter molecule. Fatty acid concentrations were quantified as above. Table 15 shows higher odd chain fats in those strains having the ability to use propionic acid as a starter. The third strain HWK201(pDWPT) produced lower levels of odd chain fatty acid implying the importance of the four genes (plasmid pHWABTZ) for better fatty acid

TABLE 14

Concentration of branched chain fatty acid production of strains HWK201 (pWL1T), HWK201 (pDWPT) and HWK201 (pBAD33)

| Strain | Relevant genotype | Arabinose (mM) | Isobutyrate (g/L) | Concentration of branched fatty acid (mg/L) at 72 h | | |
|---|---|---|---|---|---|---|
| | | | | C14 | C16 | C16:1 |
| HWK201 (pWL1T) | ΔfadD, ΔfabH, rc_TE+ | 0 | 2.64 | 8 | ND | 20 |
| HWK201 (pDWPT) | ΔfadD, ΔfabH, se_PrpE+ rc_TE+ | 10 | 2.64 | 21 | 111 | 25 |
| HWK201 (pBAD33) | ΔfadD, ΔfabH, se_PrpE+ rc_TE+ | 10 | 2.64 | — | <30 | — | rc_TE+: overexpression of acyl-ACP thioesterase from *Ricinus communis* under the TUM3 promoter in pBAD33
se_PrpE+: overexpression of propionyl-CoA synthase (prpE) from *Salmonella enterica*
ΔfadD: deactivation of acyl-CoA synthetase
ΔfabH: deactivation of β-ketoacyl-acyl carrier protein synthase III Odd Chain Fatty Acid Production The versatility of the KASIII independent synthesis pathway was demonstrated by using propionic acid to produce odd chain fatty acids. The priming molecule (propionyl production. Furthermore, the fourth strain HWK201 (pDW1T) did not produce detectable quantity of odd chain fatty acid showing the importance of the four genes (plasmid pHWABTZ) as well as the prpE gene for better fatty acid production.

TABLE 15

Concentration of odd and even chain fatty acid production of strains HWK201 (pHWABTZ, pDWPT), HWK201 (pHWABTC pDWPT), HWK201 (pW1T) and HWK201 (pDWPT)

| Strain | Relevant genotype | IPTG (mM)/ Arabinose (mM) | Propionic acid (g/L) | Concentration of odd and even fatty acid (mg/L) at 72 h | | |
|---|---|---|---|---|---|---|
| | | | | C15 | C16 | C16:1 |
| HWK201 (pHWABTZ pDWPT) | ΔfadD, ΔfabH, re_PhaA+, re_PhaB+, td_TER+, | 0.05/10 | 0.89 | 158 | 127 | 18 |

TABLE 15-continued

Concentration of odd and even chain fatty acid production of strains HWK201 (pHWABTZ, pDWPT), HWK201 (pHWABTC pDWPT), HWK201 (pW1T) and HWK201 (pDWPT)

| Strain | Relevant genotype | IPTG (mM)/ Arabinose (mM) | Propionic acid (g/L) | Concentration of odd and even fatty acid (mg/L) at 72 h | | |
|---|---|---|---|---|---|---|
| | | | | C15 | C16 | C16:1 |
| HWK201 (pHWABTC pDWPT) | ec_FabZ$^+$, se_PrpE$^+$, rc_TE$^+$ ΔfadD, ΔfabH, re_PhaA$^+$, re_PhaB$^+$, td_TER$^+$, ca_CRT$^+$, se_PrpE$^+$, rc_TE$^+$ | 0.05/10 | 0.89 | 25 | 40 | 0 |
| HWK201 (pDWPT) | ΔfadD, ΔfabH, se_PrpE$^+$ rc_TE+ | 0/10 | 0.89 | 46 | 161 | 22 |
| HWK201 (pW1T) | ΔfadD, ΔfabH, rc_TE+ | 0/0 | 0.89 | ND | 29 | 41 | re_PhaA$^+$: overexpression of β-ketothiolase from *Ralstonia eutropha* H16 in pTrc99a
re_PhaB$^+$: overexpression of acetoacelyl-CoA reductase from *Ralstonia eutropha* H16 in pTrc99a
td_TER$^+$: overexpression of trans-enoyl-coenzyme A reductase from *Treponema denticola* in pTrc99a
ec_FabZ$^+$: overexpression of 3-hydroxyacyl-ACP dehydrase from *E. coli* in pTrc99a
rc_TE$^+$: overexpression of acyl-ACP thioesterase from *Ricinus communis* under the TUM3 promoter in pBAD33
se_PrpE$^+$: overexpression of propionyl-CoA synthase (prpE) from *Salmonella enterica*
ΔfadD: deactivation of acyl-CoA synthetase
ΔfabH: deactivation of β-ketoacyl-acyl carrier protein synthase III Prophetic: Omega Amino Fatty Acid Production The versatility of the KASIII independent synthesis pathway can be demonstrated by using a different substrate to produce omega amino fatty acids. The ability to synthesize omega-functionalized fatty acid is demonstrated by supplying the substrate beta-alanine. The CoA activated primer molecule can either be provided by the native or engineered in vivo pathways or from externally added molecules, but in this case the priming molecule (beta-alanyl CoA) is supplied by the activation of externally added beta-alanine using propionyl-CoA synthase (prpE) from *Salmonella enterica*.

The beta-alanyl CoA was then extended to longer chain fatty acid with an omega amino group by the FAS cycle (similar to that shown in FIG. 13). The plasmid pDWPT, which carries the acyl-ACP thioesterase from *Ricinus communis* and propionyl-CoA synthase (prpE) from *Salmonella enterica* is used (similar to FIG. 14).

A single colony of strain HWK201 (pHWABTZ, pDWPT), HWK201 (pTrc99a, pDWPT), HWK201 (pDWPT) is inoculated into 5 ml of LB and the experiment proceeds as described above.

Prophetic: Changing Chain Length

The versatility of the KASIII independent synthesis pathway to produce fatty acid with various carbon chain lengths can be demonstrated by using different acyl-ACP thioesterases with various substrate specificity. In this experiment, the biosynthesis of fatty acids with a TE specific to shorter carbon chain length, dodecanoic acid (C12), is used. The acyl-ACP thioesterase from *Ricinus communis* under the TUM3 promoter in pBAD33 (plasmid pWL4T) is replaced with the California Bay Tree (M94159.1) TE. The plasmid constructs are named pWL4T-CB12 and pWL4T-BS12.

A single colony of strain HWK201 (pHWABTZ, pWL4T-CB12) or HWK201 (pHWABTZ, pWL4T-BS12) is inoculated into 5 ml of LB and the experiment proceeds as described above. Although data is not yet available herein, our lab has already demonstrated the ability to control fatty acid length by judicious selection of the TE. Thus, proof of concept is already available.

Prophetic: Hydroxyfatty Acids

The biosynthesis of hydroxy fatty acid can be used to demonstrate the ability of synthesizing hydroxy fatty acids with the KASIII-independent fatty acid synthesis system with various TEs with differing substrate specificity. In addition, a priming molecule (glycolyl CoA) is supplied by the activation of externally added glycolic acid using propionyl-CoA synthase (prpE) from *Salmonella enterica*. In this experiment, we will use the 3-hydroxyacyl-ACP dehydrase from *E. coli* (ec FabZ) instead of crotonase. Plasmid pDWPT-CB12 is constructed by replacing the acyl-ACP thioesterase from *Ricinus communis* with that from the California Bay Tree and propionyl-CoA synthase (prpE) from *Salmonella enterica*.

A single colony of strain HWK201 (pHWABTZ, pDWPT-CB12) or HWK201 (pWL1T) is inoculated into 5 ml of LB and the experiments proceed as described. Data is not shown, but preliminary results indicate likely success.

Prophetic: Halogenated Fatty Acids

The versatility of the KASIII independent synthesis pathway can also be demonstrated by using a different substrate to produce halogenated fatty acids. The priming molecule chloroacetic acid or chloropropionic acid is supplied by the activation of externally added chloroacetic/chloropropionic acid using propionyl-CoA synthase (prpE) from *Salmonella enterica*. The chloroacyl-CoA is then extended to longer chain fatty acid with an omega chloro-group by the FAS cycle (similar to that shown in FIG. 13). The plasmid pHWABTZ carrying the genes re phaA, re phaB, td ter, ec fabZ which encode for enzymes converts chloroacetyl-CoA to chlorobutyryl-CoA or a similar compound for the chloropropionoyl-CoA. In addition, the plasmid pDWPT, which carries the acyl-ACP thioesterase from *Ricinus communis* and propionyl-CoA synthase (prpE) from *Salmonella enterica*, is used (similar to FIG. 14).

A single colony of strain HWK201 (pHWABTZ, pDWPT) or HWK201 (pDWPT) is inoculated into 5 ml of Luria-Bertani (LB) and the experiment proceeds as above. Since the FAS enzymes are very forgiving of substrate specificity, this is predicted to be successful.

Prophetic: Omega Unsaturated Fats

In this experiment, the biosynthesis of omega unsaturated acids is used to demonstrate the ability of synthesizing omega functionalized fatty acid by supplying a proper primer substrate. Propenoyl-CoA is supplied by the activation of externally added acrylic acid using propionyl-CoA synthase (prpE) from *Salmonella enterica*. The propenoyl-CoA is then extended to longer chain fatty acid with omega unsaturated group by the FAS cycle (similar to that shown in FIG. 13). The plasmid pHWABTZ carrying the genes re phaA, re phaB, td ter, ec fabZ produces enzymes to convert propenoyl-CoA to pentenoyl-CoA. In addition, the plasmid pDWPT, which carries the acyl-ACP thioesterase from *Ricinus communis* and propionyl-CoA synthase (prpE) from *Salmonella enterica*, is used (similar to FIG. 14).

A single colony of strain HWK201 (pHWABTZ, pDWPT) or HWK201 (pDWPT) is inoculated into 5 ml of LB and the experiment proceeds as described above.

Prophetic: Using Different Genes to Initiate the FAS

Figure 9:
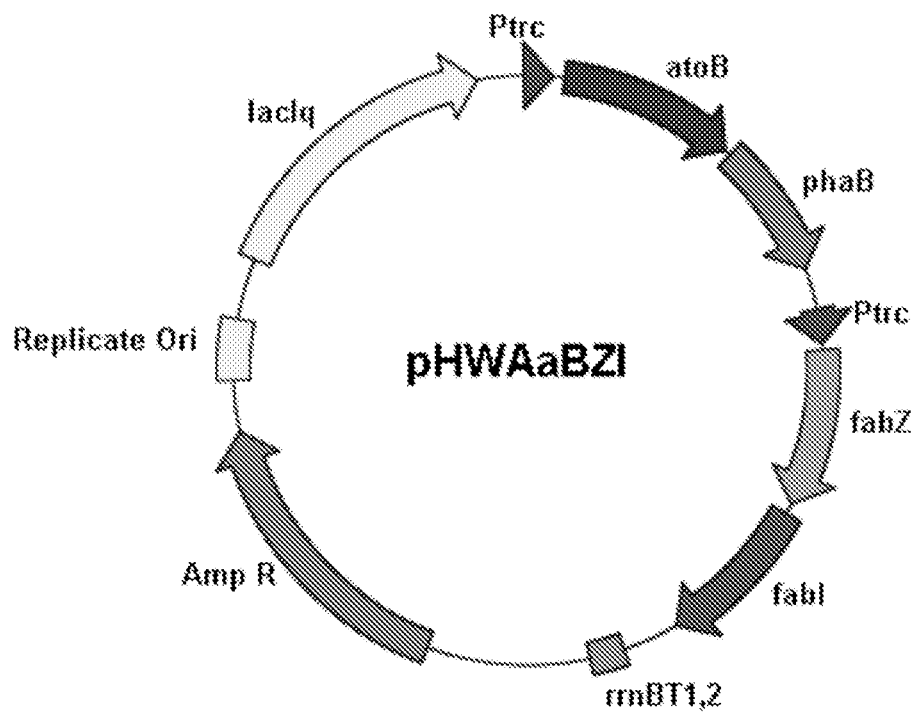
FIG. 9: Schematic diagram of pHWAaBZI. Abbreviations: atoB gene from *E. coli*; phaB gene from *Ralstonia eutropha* H16; fabZ gene from *E. coli*; fabI gene from *E. coli*; pTrc, trc promoter; lad, lac operon repressor; Amp, ampicillin resistant gene; pBR322 origin, origin of replication of plasmid pBR322, rrnBT1,2, transcriptional terminator of rrnB.

FIG. 9 is a schematic diagram of the plasmid pHWAaBZI. This plasmid is shown to be able to replace plasmid pHWABTZ to extend two or three-carbon primer molecule to longer carbon chain length molecules, which will then enter the FAS cycle and be elongated until release by an overexpressed TE. As above, chain length can be specified by selecting the appropriate TE. A single colony of strain HWK201 (pHWAaBZI, pDWPT) is inoculated into 5 ml of LB and the experiment proceed as described above.

Prophetic: A,Ω-Dicarboxylic Acids

The ω-hydroxy fatty acids produced above can be further converted to α,ω-dicarboxylic acids by converting the hydroxyl group to the carboxylic group using AlkH and AlkJ from *Pseudomonas putida* P1. At least three configurations can be envisioned. First, the genes expressing AlkH and AlkJ from *Pseudomonas putida* P1 can be also included in the engineered cells described above. Thus, the ω-hydroxy fatty acids produced will be converted to α,ω-dicarboxylic acids within the same cell. In the second configuration, co-culturing of the engineered cells described above together with cells carrying the genes expressing AlkH and AlkJ from *Pseudomonas putida* P1 will allow the same reactions on fats that are released from the first cells and taken up by the second. In the third two-step configuration, the ω-hydroxy fatty acids produced by the engineered cells described in above will be disrupted to release the ω-hydroxy fatty acids before feeding into a culture of cells carrying the genes expressing AlkH and AlkJ from *Pseudomonas putida* P1.

Although this experiment has not yet been completed, proof of concept has been demonstrated by the successful use of the AlkH and AlkJ genes to convert fats made by the regular FAS cycle or the reverse beta-oxidation cycle.

Prophetic: *Bacillus*

The above experiments are repeated in *Bacillus subtilis*. The same genes can be used, especially since *Bacillus* has no significant codon bias. A protease-deficient strain like WB800N is preferably used for greater stability of heterologous protein. The *E. coli*-*B. subtilis* shuttle vector pMTLBS72 exhibiting full structural stability can be used to move the genes easily to a more suitable vector for *Bacillus*. Alternatively, two vectors pHT01 and pHT43 allow high-level expression of recombinant proteins within the cytoplasm. As yet another alternative, plasmids using the theta-mode of replication such as those derived from the natural plasmids pAMβ1 and pBS72 can be used. Several other suitable expression systems are available. Since the FAS genes are ubiquitous, the invention is predicted to function in *Bacillus*, as well as other bacteria having Type II FAS enzymes.

Prophetic: Yeast

Standard cloning/metabolic engineering approaches can be used to implement the KASIII-independent approach in yeast. In fact, transplanting the whole native *E. coli* FAS system to yeast has recently been reported, indicating proof of concept for using the bacterial FAS cycle in yeast.

There are many shuttle vectors for moving genes into yeast. Indeed, almost all commonly used *S. cerevisiae* vectors are shuttle vectors. Yeast shuttle vectors have components that allow for replication and selection in both *E. coli* cells and yeast cells. For example, the pAUR vector series by ClonTech® includes six *E. coli*-yeast shuttle vectors, each constructed for a particular application in either *Saccharomyces cerevisiae*, *Schizosaccharomyces*, *Saccharomyces pombe* or *Aspergillus nidulans*. The vectors include a novel drug-resistance selective marker that confers Aureobasidin A resistance in transformed yeast or filamentous fungal species.

Fine-tuning of the KASIII-independent approach system, such as codon optimization, promoter strength manipulation through RBS design, and protein engineering can be adapted to improve the system performance to increase the product titer and yield. Since various TE and FAS enzymes have already been successfully transformed into yeast, success is predicted.

The following references are incorporated by reference in their entirety for all purposes:

Zhang X., Li M., Agrawal A., San K. Efficient free fatty acid production in *Escherichia coli* using plant acyl-ACP thioesterases. Metab. Eng. 2011, 13: 713-722.

Nathan L. Alderson, et al., The Human FA2H Gene Encodes a Fatty Acid 2-Hydroxylase. J. Biol. Chem. 2004, 279: 48562-48568.

N. Nakashima & T. Tamura. Gene silencing in *Escherichia coli* using antisense RNAs expressed from doxycycline-inducible vectors. Letters in Applied Microbiology. 2013, 56: 436-442.

Jaoon Y. H. Kim & Hyung Joon Cha. Down-regulation of acetate pathway through antisense strategy in *Escherichia coli*: improved foreign protein production. Biotechnol Bioeng, 2003, 83(7): 841-853.

Srivastava A., et al, 14-Aminotetradecanoic acid exhibits antioxidant activity and ameliorates xenobiotics-induced cytotoxicity. Mol. Cell. Biochem. 2012, 364: 1-9.

Jing, et al., Phylogenetic and experimental characterization of an acyl-ACP thioesterase family reveals significant diversity in enzymatic specificity and activity, BMC Biochemistry 2011, 12:44.

U.S. Pat. No. 8,906,667 Increasing NADPH-dependent products

US20140273114 bacteria and method for synthesizing fatty acids

U.S. Pat. No. 8,795,991 Increasing bacterial succinate productivity

US20140212935 Short chain fatty acids from bacteria

US20140193867 Microbial odd chain fatty acids

U.S. Pat. No. 8,709,753 Native NAD-dependent GAPDH replaced with NADP-dependent GAPDH plus NADK US20140093921 Bacteria and method for synthesizing fatty acids U.S. Pat. No. 8,486,686 Large scale microbial culture method U.S. Pat. No. 8,236,525 Reduced phosphotransferase system activity in bacteria U.S. Pat. No. 7,901,924 Increased bacterial CoA and acetyl-CoA pools U.S. Pat. No. 7,709,261 Recycling system for manipulation of intracellular NADH availability

The invention claimed is:

1. A genetically engineered microbe comprising:
a) a β-ketoacyl-acyl carrier protein synthase III (KASIII) independent fatty acid synthesis (FAS) pathway that makes a product from a primer excluding acetyl coA or propionyl-coA using FAS enzymes (except for KASIII);
b) said microbe having an overexpressed acyl ACP thioesterase (TE);
c) said microbe also having one or more expression vectors overexpressing enzymes selected from the group consisting of 3-ketoacyl-ACP synthetase, 3-ketoacyl-ACP reductase, 3-hydroxyacyl ACP dehydrase, enoyl-ACP reductase, and Co-A transferase;
d) said microbe comprising reduced KASIII activity (KASIII$^-$) or null KASIII activity (ΔKASIII); and
e) said microbe having one or more expression vectors overexpressing beta-ketothiolase, acetoacetyl-CoA reductase, trans-enoyl-CoA reductase, and either 3-hydroxyacyl-[ACP] dehydratase or crotonase.

2. A method of making a product, comprising: a) growing the microbe of claim 1 in a medium allowing cell growth; b) elongating a starter molecule or primer molecule having 2 or >2 carbons using the FAS enzymes (except for KASIII) to make a product; and, c) isolating said product.

3. A method of making a product, comprising: a) growing the microbe of claim 1 in a medium allowing cell growth; b) elongating a starter molecule or primer molecule having >2 carbons using the FAS enzymes (except for KASIII) to make a product; and, c) isolating said product.

4. The method of claim 3, wherein said product is selected from the group consisting of C6-C16 hydroxy fatty acids, C6-C16 amino fatty acids, C6-C16 halogenated fatty acids, C6-C16 branched fatty acids, C6-C16 unsaturated fatty acids, C6-C16 ω-hydroxy fatty acids, C6-16 α,ω-dicarboxylic acids, C6-16 α,ω-diol fatty acids or derivatives thereof.

5. The method of claim 3, wherein said product is C6-C16 ω-hydroxy fatty acids or derivatives thereof.

6. The method of claim 5, wherein bifunctional α,ω-dicarboxylic acids are obtained by the oxidation of said ω-hydroxy fatty acids.

7. The method of claim 5, wherein bifunctional α,ω-diols are obtained by the reduction of said ω-hydroxy fatty acids.

8. A genetically engineered microbe having a β-ketoacyl-acyl carrier protein synthase III (KASIII) independent fatty acid synthesis (FAS) pathway that makes a product from a starter molecule of >2 carbons or >3 carbons, said starter molecule excluding acetyl-CoA or propionyl-coA, using FAS enzymes (except for KASIII), said microbe having reduced KASIII activity, an overexpressed acyl ACP thioesterase (TE), and reduced native acyl-carrier protein (ACP) dependent fatty acid biosynthesis, malonyl-CoA-ACP transacylase, and acetyl-CoA carboxylase.

9. A method of making a product; a) growing the microbe of claim 8 in a medium; b) elongating a coA-activated starter molecule having >2 carbons using the FAS enzymes to make a product; and, c) isolating said product.

10. The method of claim 9, further comprising adding said starter molecule to said medium.

11. The microbe of claim 8, having one or more overexpressed enzymes selected from the group consisting of 3-ketoacyl-ACP synthetase, 3-ketoacyl-ACP reductase, 3-hydroxyacyl ACP dehydrase, enoyl-ACP reductase, thioesterase or Co-A transferase.

12. The microbe of claim 11, wherein said starter molecule is produced in vivo by a native pathway or by a genetically engineered pathway.

13. A method of making a product; a) growing the microbe of claim 11 in a medium; b) elongating a coA-activated starter molecule having >2 carbons using the FAS enzymes to make a product; and, c) isolating said product.

14. The microbe of claim 8, wherein said starter molecule is produced in vivo by a native pathway or by a genetically engineered pathway.

15. A method of making a product; a) growing the microbe of claim 14 in a medium; b) elongating a coA-activated starter molecule having >2 carbons using the FAS enzymes to make a product; and, c) isolating said product.

16. A recombinant bacteria comprising KASIII$^-$ (β-ketoacyl-acyl carrier protein synthase III$^-$), TE$^+$ (thioesterase$^+$), PhaA$^+$ (beta-ketothiolase$^+$), PhaB$^+$ (acetoacetyl-CoA reductase$^+$), TER$^+$ (trans-enoyl-CoA reductase$^+$), and either FabZ$^+$ (3-hydroxyacyl-[acyl-carrier-protein] dehydratase$^+$) or crt$^+$ (crotonase$^+$).

17. The bacteria of claim 16, further comprising PrpE$^+$ (propionyl-CoA synthase).

* * * * *